US008821015B2

(12) United States Patent
Stagnitto et al.

(10) Patent No.: US 8,821,015 B2
(45) Date of Patent: Sep. 2, 2014

(54) ALIGNMENT APPARATUS FOR X-RAY IMAGING SYSTEM

(75) Inventors: Joseph E. Stagnitto, Rochester, NY (US); Xiaohui Wang, Pittsford, NY (US); Michael C. Lalena, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 441 days.

(21) Appl. No.: 13/283,654

(22) Filed: Oct. 28, 2011

(65) Prior Publication Data

US 2012/0230473 A1 Sep. 13, 2012

Related U.S. Application Data

(60) Provisional application No. 61/450,260, filed on Mar. 8, 2011, provisional application No. 61/533,396, filed on Sep. 12, 2011.

(51) Int. Cl.
*A61B 6/08* (2006.01)
*A61B 6/00* (2006.01)

(52) U.S. Cl.
CPC .............. *A61B 6/4405* (2013.01); *A61B 6/4291* (2013.01); *A61B 6/08* (2013.01); *A61B 6/465* (2013.01); *A61B 6/588* (2013.01); *A61B 6/587* (2013.01)
USPC ......................................................... 378/205

(58) Field of Classification Search
CPC .................... G01R 33/00; A61B 6/587–6/589; A61B 6/40; A61B 6/06; A61B 6/42; A61B 6/44; A61B 6/02; A61B 6/10; A61B 6/14; A61B 6/46; A61B 6/56; A61B 8/13–8/15; A61B 6/08
USPC .............. 378/205–207; 324/207.11, 327–329
See application file for complete search history.

(56) References Cited

U.S. PATENT DOCUMENTS 4,017,858 A 4/1977 Kuipers
4,054,881 A 10/1977 Raab
(Continued)

FOREIGN PATENT DOCUMENTS

JP 2000-023955 1/2000
WO WO 2007149402 A2 * 12/2007

OTHER PUBLICATIONS

One-page brochure for EasyPos dental x-ray positioning system from website, Mar. 2010. hyphendev.fr file PubEasypos08v3.pdf.
(Continued)

*Primary Examiner* — Toan Ton
*Assistant Examiner* — John Corbett

(57) ABSTRACT

A method for aligning a radiation source with a portable image receiver in a radiographic imaging system generates a magnetic field with a predetermined field pattern and with a time-varying vector direction at a predetermined frequency from an emitter apparatus that is coupled to the radiation source, wherein the generated magnetic field further comprises a synchronization signal. Sensed signals from the magnetic field are obtained from a sensing apparatus that is coupled to the image receiver, wherein the sensing apparatus comprises three or more sensor elements, wherein at least two of the sensor elements are arranged at different angles relative to each other and are disposed outside the imaging area of the image receiver. An output signal is indicative of an alignment adjustment according to the amplitude and phase of the obtained sensed signals relative to the synchronization signal.

20 Claims, 37 Drawing Sheets

(56) References Cited

U.S. PATENT DOCUMENTS

| | | | |
|---|---|---|---|
| 4,246,486 A | 1/1981 | Madsen |
| 4,752,948 A | 6/1988 | MacMahon |
| 4,836,671 A | 6/1989 | Bautista |
| 5,241,578 A | 8/1993 | MacMahon |
| 5,388,143 A | 2/1995 | MacMahon |
| 5,539,798 A | 7/1996 | Asahina et al. |
| 5,550,889 A | 8/1996 | Gard et al. |
| 5,617,462 A | 4/1997 | Spratt |
| 5,646,525 A * | 7/1997 | Gilboa ................ 324/207.17 |
| 5,751,783 A | 5/1998 | Granfors et al. |
| 5,949,811 A | 9/1999 | Baba et al. |
| 6,154,522 A | 11/2000 | Cumings |
| 6,192,105 B1 | 2/2001 | Hunter et al. |
| 6,404,851 B1 | 6/2002 | Possin et al. |
| 6,422,750 B1 | 7/2002 | Kwasnick et al. |
| 6,702,459 B2 | 3/2004 | Barnes et al. |
| 6,760,405 B2 | 7/2004 | Ruetten et al. |
| 6,944,266 B2 | 9/2005 | Yamazaki et al. |
| 6,950,492 B2 | 9/2005 | Besson |
| 7,156,553 B2 | 1/2007 | Tanaka et al. |
| 7,368,724 B2 | 5/2008 | Morii et al. |
| 7,490,986 B2 | 2/2009 | Takekoshi et al. |
| 7,519,155 B2 | 4/2009 | Mollus et al. |
| 7,581,884 B1 | 9/2009 | Barnes et al. |
| 7,601,961 B2 | 10/2009 | Franklin et al. |
| 7,632,016 B1 | 12/2009 | Huang et al. |
| 7,780,350 B2 | 8/2010 | Tranchant et al. |
| 7,794,144 B2 | 9/2010 | Windt |
| 7,798,710 B1 | 9/2010 | Barnes et al. |
| 2002/0150215 A1 | 10/2002 | Barnes et al. |
| 2003/0165216 A1 | 9/2003 | Walker et al. |
| 2004/0101100 A1 | 5/2004 | Morii et al. |
| 2004/0105526 A1 | 6/2004 | Zhang et al. |
| 2005/0058244 A1 | 3/2005 | Tanaka et al. |
| 2005/0077085 A1 * | 4/2005 | Zeller et al. ................ 175/45 |
| 2006/0269114 A1 | 11/2006 | Metz |
| 2007/0030957 A1 | 2/2007 | Pommi |
| 2007/0244388 A1 | 10/2007 | Sato et al. |
| 2007/0255087 A1 | 11/2007 | Minai |
| 2007/0297569 A1 | 12/2007 | Saunders |
| 2008/0130837 A1 | 6/2008 | Heath et al. |
| 2008/0204012 A1 | 8/2008 | Krueger et al. |
| 2009/0032744 A1 * | 2/2009 | Kito et al. ................ 250/580 |
| 2009/0060145 A1 | 3/2009 | Tranchant et al. |
| 2009/0086926 A1 | 4/2009 | Wang et al. |
| 2010/0002831 A1 | 1/2010 | Maack |

OTHER PUBLICATIONS

International Search Report & Written Opinion, International application No. PCT/US2011/032035, dated Dec. 20, 2011, 9 pages.
International Search Report & Written Opinion, International application No. PCT/US2011/032020, date Nov. 28, 2011, 8 pages.
International Search Report, International application No. PCT/US2012/0262212, dated Aug. 30, 2012, 2 pages.

* cited by examiner

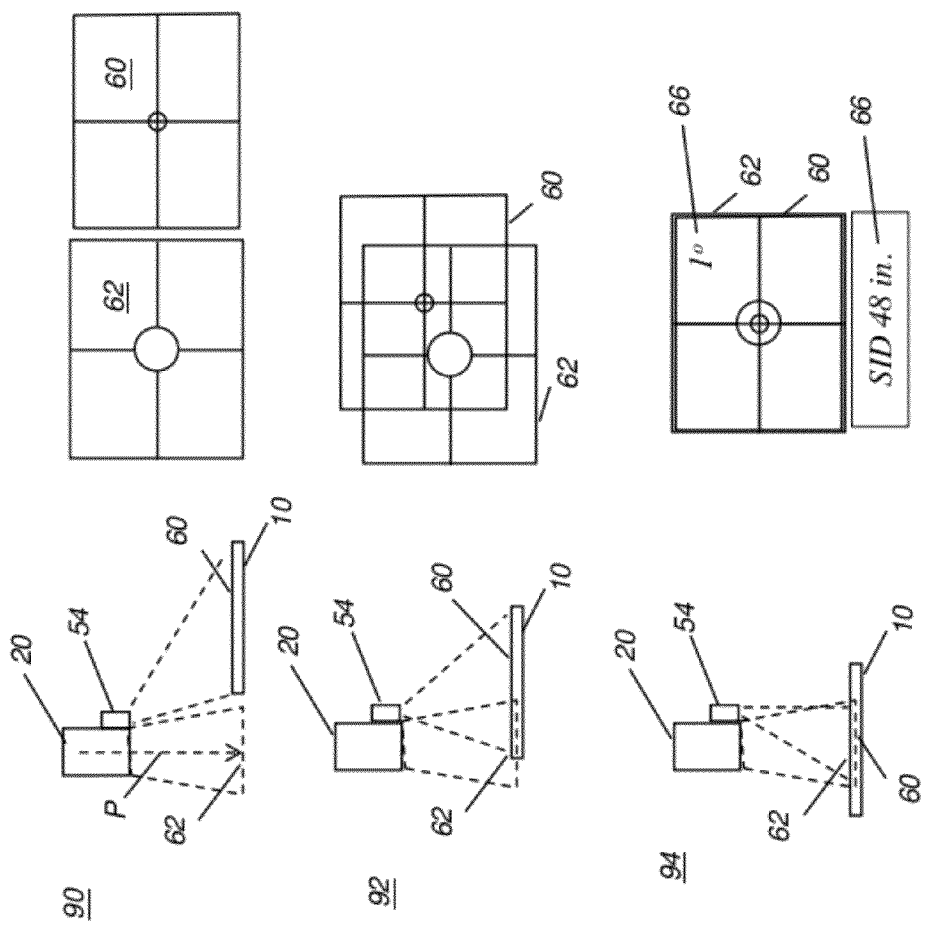

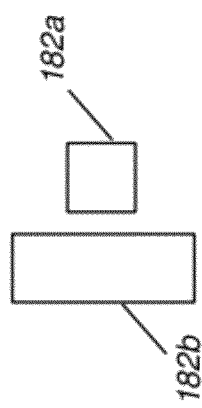
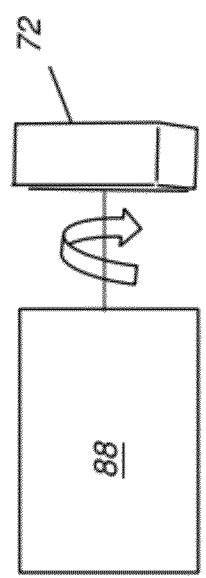
FIG. 12C
FIG. 12B

ALIGNMENT APPARATUS FOR X-RAY IMAGING SYSTEM

CROSS-REFERENCE TO RELATED APPLICATIONS

This is a 35 U.S.C 111a application that claims the benefit of U.S. Provisional Application Ser. No. 61/450,260, filed 8 Mar. 2011, entitled "ALIGNMENT METHOD FOR X-RAY IMAGING," by Joseph Stagnitto and of U.S. Provisional Application Ser. No. 61/553,396, filed 12 Sep. 2011, entitled "ALIGNMENT APPARATUS FOR X-RAY IMAGING SYSTEM" by Joseph Stagnitto et al.

FIELD OF THE INVENTION

This invention generally relates to an apparatus for radiation imaging and more particularly relates to a positioning apparatus for providing proper alignment of the radiation source relative to an image detection device for recording a radiation image.

BACKGROUND OF THE INVENTION

When an x-ray image is obtained, there is generally an optimal alignment between the radiation source and the two dimensional receiver that records the image data. In most cases, it is preferred that the x-ray source provide radiation in a direction that is perpendicular to the surface of the recording medium. For this reason, large-scale radiography systems mount the radiation head and the recording medium holder at a specific angle relative to each other. Orienting the head and the receiver typically requires a mounting arm of substantial size, extending beyond the full distance between these two components. With such large-scale systems, unwanted tilt or skew of the receiver is thus prevented by the hardware of the imaging system itself.

With the advent of mobile or portable radiation imaging apparatus, such as those used in Intensive Care Unit (ICU) environments, a fixed angular relationship between the radiation source and two-dimensional radiation receiver is no longer imposed by the mounting hardware of the system itself. Instead, an operator is required to aim the radiation source toward the receiver surface, providing as perpendicular an orientation as possible, typically using a visual assessment.

In computed radiography (CR) systems, the two-dimensional image-sensing device itself is a portable cassette that stores the readable imaging medium. In direct digital radiography (DR) systems, the two-dimensional image-sensing device is a portable digital detector with either flat, rigid, or flexible substrate support.

FIG. 1 shows a mobile x-ray apparatus that can be employed for computed radiography (CR) and/or digital radiography (DR). A mobile radiography unit 600 has a frame 620 that includes a display 610 for display of obtained images and related data and a control panel 612 that allows functions such as storing, transmitting, modifying, and printing of the obtained image. For mobility, unit 600 has one or more wheels 615 and one or more handle grips 625, typically provided at waist-, arm-, or hand-level, that help to guide unit 600 to its intended location. A self-contained battery pack 626 can provide a power source, eliminating the need for operation near a power outlet.

Mounted to frame 620 is a support member 635 that supports an x-ray source 640, also termed an x-ray tube, tube head, or generator mounted on a boom apparatus, more simply termed a boom 70. In the embodiment shown, support member 635 has a vertical column 64 of fixed height. Boom 70 extends outward a variable distance from support member 635 and rides up and down column 64 to the desired height for obtaining the image on a portable receiver 10. Boom 70 may extend outward by a fixed distance or may be extendible over a variable distance. Height settings for the x-ray source 640 can range from low height for imaging feet and lower extremities to shoulder height and above for imaging the upper body portions of patients in various positions. In other embodiments, the support member for the x-ray source is not a fixed column, but is rather an articulated member that bends at a joint mechanism to allow movement of the x-ray source over a range of vertical and horizontal positions.

In computed radiography (CR) systems, the two-dimensional image-sensing receiver 10 is a portable cassette that stores the readable imaging medium. In direct digital radiography (DR) systems, the two-dimensional image-sensing receiver 10 is a portable digital detector with either flat, rigid, or flexible substrate support. Receiver 10, however, because it is portable, may not be visible to the technician once it is positioned behind the patient. This complicates the alignment task for portable systems, requiring some method for measuring source-to-image distance (SID), tilt angle, and centering, and making it more difficult to use a grid effectively for reducing the effects of scatter. Because of this added complexity with a portable radiography system, the technician may choose not to use a grid; the result without a grid, however, is typically a lower-quality image.

There have been a number of approaches to the problem of providing methods and tools to assist operator adjustment of x-ray source-to-receiver angle. One conventional approach has been to provide mechanical alignment in a more compact fashion, such as that described in U.S. Pat. No. 4,752,948 entitled "Mobile Radiography Alignment Device" to MacMahon. A platform is provided with a pivotable standard for maintaining alignment between an imaging cassette and radiation source. However, complex mechanical solutions of this type tend to reduce the overall flexibility and portability of these x-ray systems. Another type of approach, such as that proposed in U.S. Pat. No. 6,422,750 entitled "Digital X-ray Imager Alignment Method" to Kwasnick et al. uses an initial low-exposure pulse for detecting the alignment grid; however, this method would not be suitable for portable imaging conditions where the receiver must be aligned after it is fitted behind the patient.

Other approaches project a light beam from the radiation source to the receiver in order to achieve alignment between the two. Examples of this approach include U.S. Pat. No. 5,388,143 entitled "Alignment Method for Radiography and Radiography Apparatus Incorporating Same" and U.S. Pat. No. 5,241,578 entitled "Optical Grid Alignment System for Portable Radiography and Portable Radiography Apparatus Incorporating Same", both to MacMahon. Similarly, U.S. Pat. No. 6,154,522 entitled "Method, System and Apparatus for Aiming a Device Emitting Radiant Beam" to Cumings describes the use of a reflected laser beam for alignment of the radiation target. However, the solutions that have been presented using light to align the film or CR cassette or DR receiver are constrained by a number of factors. The '143 and '578 MacMahon disclosures require that a fixed Source-to-Image Distance (SID) be determined beforehand, then apply triangulation with this fixed SID value. Changing the SID requires a number of adjustments to the triangulation settings. This arrangement is less than desirable for portable imaging systems that allow a variable SID. Devices using lasers, such as that described in the '522 Cumings disclosure, in some cases can require much more precision in making adjustments than is necessary.

Other examples in which light is projected from the radiation source onto the receiver are given in U.S. Pat. Nos. 4,836,671 entitled "Locating Device" to Bautista and 4,246,486 entitled "X-ray Photography Device" to Madsen. Both the Bautista '671 and Madsen '486 approaches use multiple light sources that are projected from the radiation source and intersect in various ways on the receiver.

Significantly, the solutions noted above are often of little of no value where the receiver and its accompanying grid are hidden from view, lying fully behind the patient as may be the case, for example, for chest x-ray imaging with a portable system. Today's portable radiation imaging devices allow considerable flexibility for placement of the film cassette, CR cassette, or Digital Radiography DR receiver by the radiology technician. The patient need not be in a horizontal position for imaging, but may be at any angle, depending on the type of image that is needed and on the ability to move the patient for the x-ray examination. The technician can manually adjust the position of both the portable cassette or receiver and the radiation source independently for each imaging session. Thus, it can be appreciated that an alignment apparatus for obtaining the desired angle between the radiation source and the grid and image receiver must be able to adapt to whatever orientation is best suited for obtaining the image. Tilt sensing, as has been conventionally applied and as is used in the device described in U.S. Pat. No. 7,156,553 entitled "Portable Radiation Imaging System and a Radiation Image Detection Device Equipped with an Angular Signal Output Means" to Tanaka et al. and elsewhere, does not provide sufficient information on cassette-to-radiation source orientation, except in the single case where the cassette lies level. More complex position sensing devices can be used, but can be subject to sampling and accumulated rounding errors that can grow worse over time, requiring frequent resynchronization.

Thus, it is apparent that conventional alignment solutions may be workable for specific types of systems and environments; however, considerable room for improvement remains. Portable radiography apparatus must be compact and lightweight, which makes the mechanical alignment approach such as that given in the '948 MacMahon disclosure less than desirable. The constraint to direct line-of-sight alignment reduces the applicability of many types of reflected light based methods to a limited range of imaging situations. The complex sensor and motion control interaction required by the Tanaka et al. '553 solution would add considerable expense, complexity, weight, and size to existing designs, with limited benefits. Many less expensive portable radiation imaging units do not have the control logic and motion coordination components that are needed in order to achieve the necessary adjustment. None of these approaches gives the operator the needed information for making a manual adjustment that is in the right direction for correcting misalignment, particularly where an anti-scatter grid is used.

A related problem is the need to achieve a source-to-image distance (SID) that is well-suited for the image to be obtained and for the grid used. Conventional alignment solutions do not provide SID information, leaving it to the technician to make separate measurements or to make an approximate SID adjustment. Moreover, conventional solutions do not provide the technician with tools to help reduce backscatter, caused by misalignment or poor adjustment of the collimator blades. This type of scatter, while not particularly problematic with other types of radiographic imaging, such as dental and mammographic imaging, can be troublesome with portable radiographic imaging apparatus, since the radiation is directed over a broad area. Radiation that works past the imaging receiver and any blocking element associated with the receiver can inadvertently be reflected back into the receiver, adversely affecting image quality. To reduce backscatter as much as possible for chest x-rays and other types of x-ray, the technician is required to estimate the location and orientation or outline of the imaging receiver and to adjust the collimator accordingly.

Significantly, none of these conventional solutions described earlier is particularly suitable for retrofit to existing portable radiography systems. That is, implementing any of these earlier solutions would be prohibitive in practice for all but newly manufactured equipment and could have significant cost impact.

Yet another problem not addressed by many of the above solutions relates to the actual working practices of radiologists and radiological technicians. A requirement for perpendicular delivery of radiation, given particular emphasis in the Tanaka et al. '553 application, is not optimal for all types of imaging. In fact, there are some types of diagnostic images for which an oblique (non-perpendicular) incident radiation angle is most desirable. For example, for the standard chest anterior-posterior (AP) view, the recommended central ray angle is oblique from the perpendicular (normal) by approximately 3-5 degrees. Conventional alignment systems, while they provide for normal incidence of the central ray, do not adapt to assist the technician for adjusting to an oblique angle.

Thus, it can be seen that there is a need for an apparatus that enables proper angular alignment and positioning of a radiation source relative to an image detection device and an optional antiscatter grid for recording a radiation image.

SUMMARY OF THE INVENTION

An object of the present invention is to advance the art of radiographic imaging by providing exemplary apparatus and methods embodiments to aid in alignment and proper positioning of the radiation source to a radiation receiver. A feature of the present invention is the use of a sensor and detector arrangement that is able to sense distance and positional orientation of the receiver relative to the radiation source. It is an advantage of certain exemplary apparatus and methods embodiments that can allow straightforward retrofitting for existing x-ray apparatus.

Exemplary apparatus and methods embodiments do not require visibility of the receiver behind the patient for alignment. It is a further advantage of one embodiment that it provides a method that can be adapted for use with a variable SID distance.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to an aspect of the present invention, there is provided a method for aligning a radiation source with a portable image receiver in a radiographic imaging system, the method can include generating a magnetic field with a predetermined field pattern and with a time-varying vector direction at a predetermined frequency from an emitter apparatus that is coupled to the radiation source, wherein the generated magnetic field further comprises a synchronization signal; obtaining sensed signals from the magnetic field from a sensing apparatus that is coupled to the image receiver, wherein the sensing apparatus comprises three or more sensor elements, wherein at least two of the sensor elements are arranged at different angles relative to each other and are disposed outside the imaging area of the image receiver; and providing an output signal indicative of an alignment adjustment according to the amplitude and phase of the obtained sensed signals relative to the synchronization signal.

BRIEF DESCRIPTION OF THE DRAWINGS

While the specification concludes with claims particularly pointing out and distinctly claiming the subject matter of the present invention, it is believed that embodiments of the invention will be better understood from the following description when taken in conjunction with the accompanying drawings, wherein:

The foregoing and other objects, features, and advantages of the invention will be apparent from the following more particular description of the embodiments of the invention, as illustrated in the accompanying drawings. The elements of the drawings are not necessarily to scale relative to each other.

FIGS. 6A and 6B are diagrams that show how projected light patterns align under various conditions, including centering, angular, and distance differences.

FIGS. 12A, 12B, and 12C are schematic diagrams that show basic distance and angular relationships that relate to signal amplitude and phase at a sensor element for an emitted magnetic field.

DETAILED DESCRIPTION OF EXEMPLARY EMBODIMENTS

Unlike the limited tilt sensing approaches that have been used in a variety of earlier radiography systems, certain exemplary apparatus and methods embodiments provide a straightforward solution to the problem of radiation source-to-receiver alignment that can be used with a number of x-ray imaging systems.

In the context of the present disclosure, the term "imaging receiver", or more simply "receiver", may include a cassette that has a photostimulable medium, such as a film or phosphor medium, for example, or may include a detector array that records an image according to radiation emitted from the radiation source. A portable receiver is not mechanically coupled to the radiation source, so that it can be easily and conveniently positioned behind the patient.

As used herein, the term "energizable" indicates a device or set of components that perform an indicated function upon receiving power and, optionally, upon receiving an enabling signal.

In the context of the present disclosure, two elements are considered to be substantially orthogonal if their angular orientations differ from each other by 90 degrees+/−12 degrees.

In the context of the present disclosure, the term "coupled" is intended to indicate a mechanical association, connection, relation, or linking, between two or more components, such that the disposition of one component affects the spatial disposition of a component to which it is coupled. For mechanical coupling, two components need not be in direct contact, but can be linked through one or more intermediary components.

Figure 1:
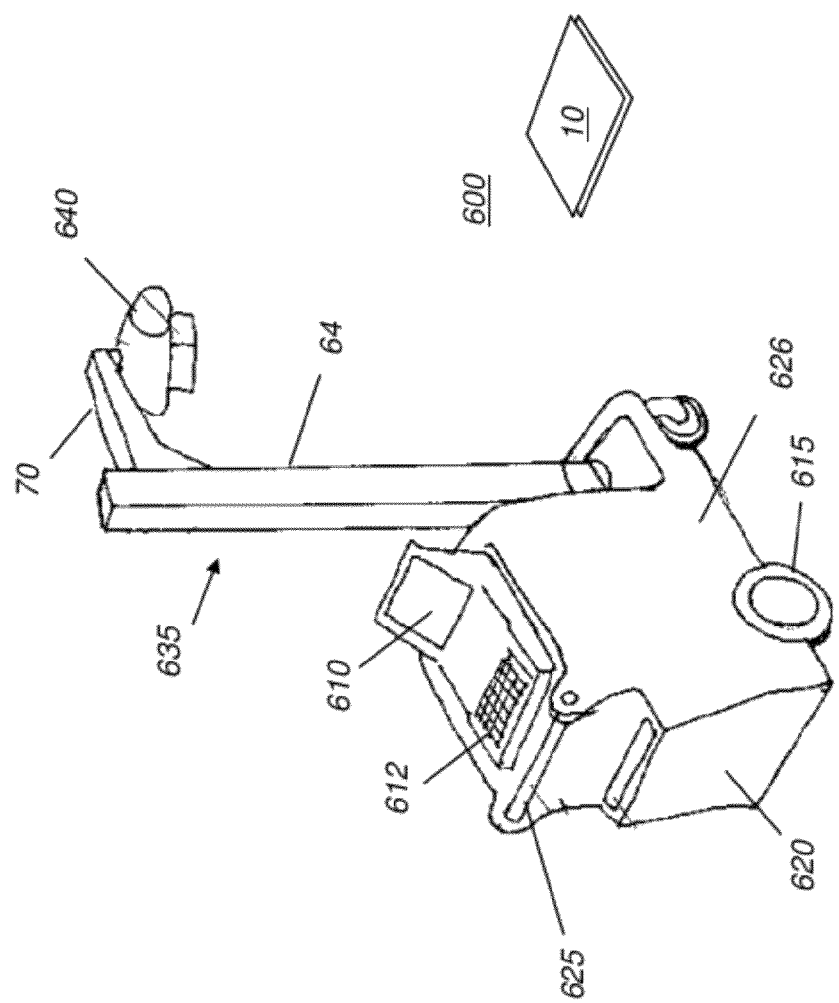
FIG. 1 shows a perspective view of one type of conventional mobile radiography unit.
Figure 2A:
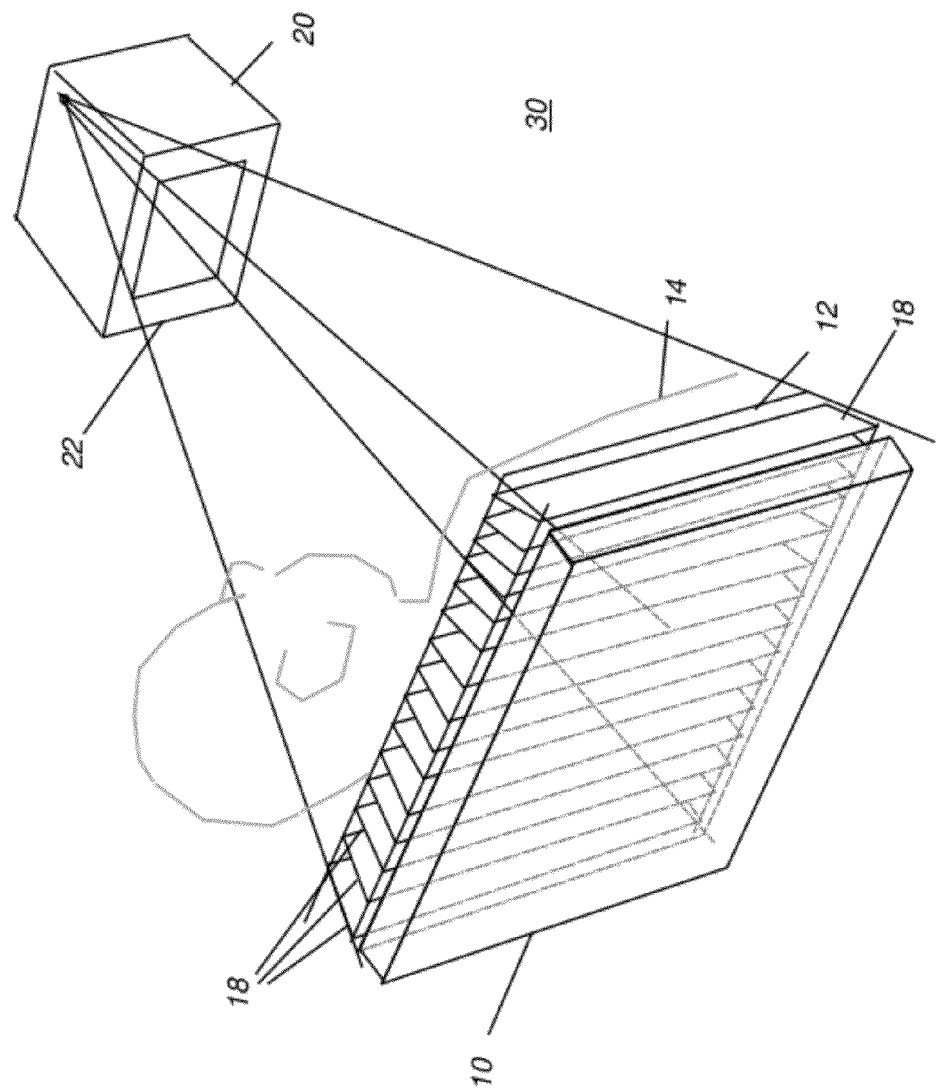
FIG. 2A is a perspective view showing the relative relationship of the patient being imaged to basic components of a diagnostic imaging apparatus.

The perspective view of FIG. 2A shows components of a radiographic imaging apparatus 30. A radiation source 20, such as an x-ray source, directs radiation toward a patient 14. A receiver 10 positioned behind the patient forms the diagnostic image from the incident radiation passing through patient 14. Receiver 10 may have a photostimulable medium, such as a film or phosphor medium, for example, or may have a detector array that records an image according to radiation emitted from radiation source 20. Receiver 10 may have landscape or portrait orientation. An optional antiscatter grid 12 has plates 18 arranged as shown in FIG. 1A, just above the surface of the receiver 10. Radiation source 20 has a collimator 22 that defines the radiation field that is directed outward from source 20, toward receiver 10 in the example of FIG. 2A.

Figure 2B:
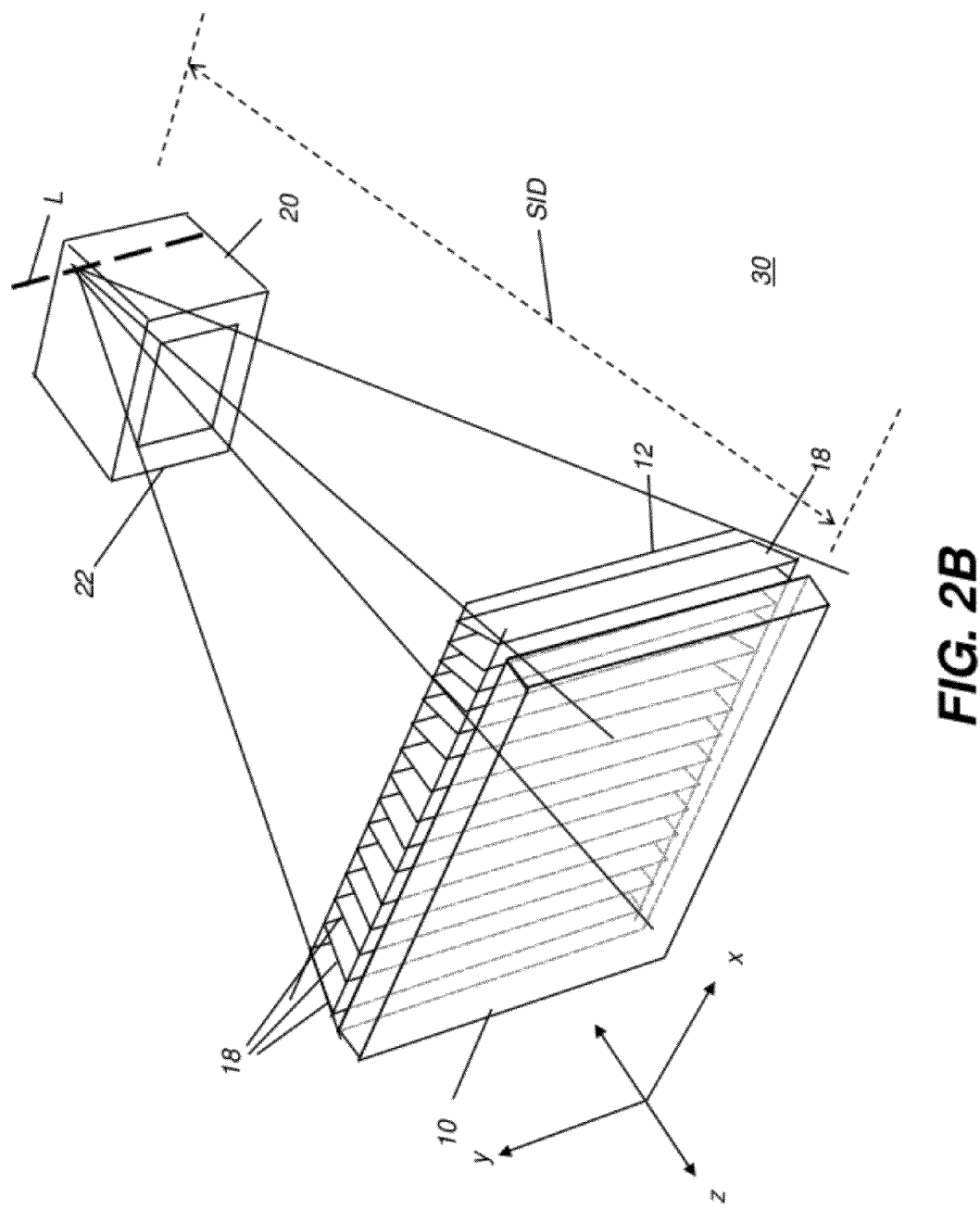
FIG. 2B is a perspective view showing important dimensional relationships for imaging system setup.

Radiation source 20 has an adjustable angular orientation for directing radiation toward receiver 10. FIG. 2B (with patient 14 not shown for better visibility of system components) shows coordinate xyz axes. Here, the source-to-image distance (SID) is in the general direction of the z axis. In FIG. 2B, radiation source 20 is in its aligned position, at a suitable SID from receiver 10. Grid plates 18 are angularly arranged so that they define a focal line L where their respective planes converge at the SID. For best alignment for most imaging in such an embodiment, radiation source 20 should be centered near focal line L and have the face portion of collimator 22 generally parallel to the planar surface of receiver 10. However, there can be image types for which a slight angular offset is preferred.

Figure 2C:
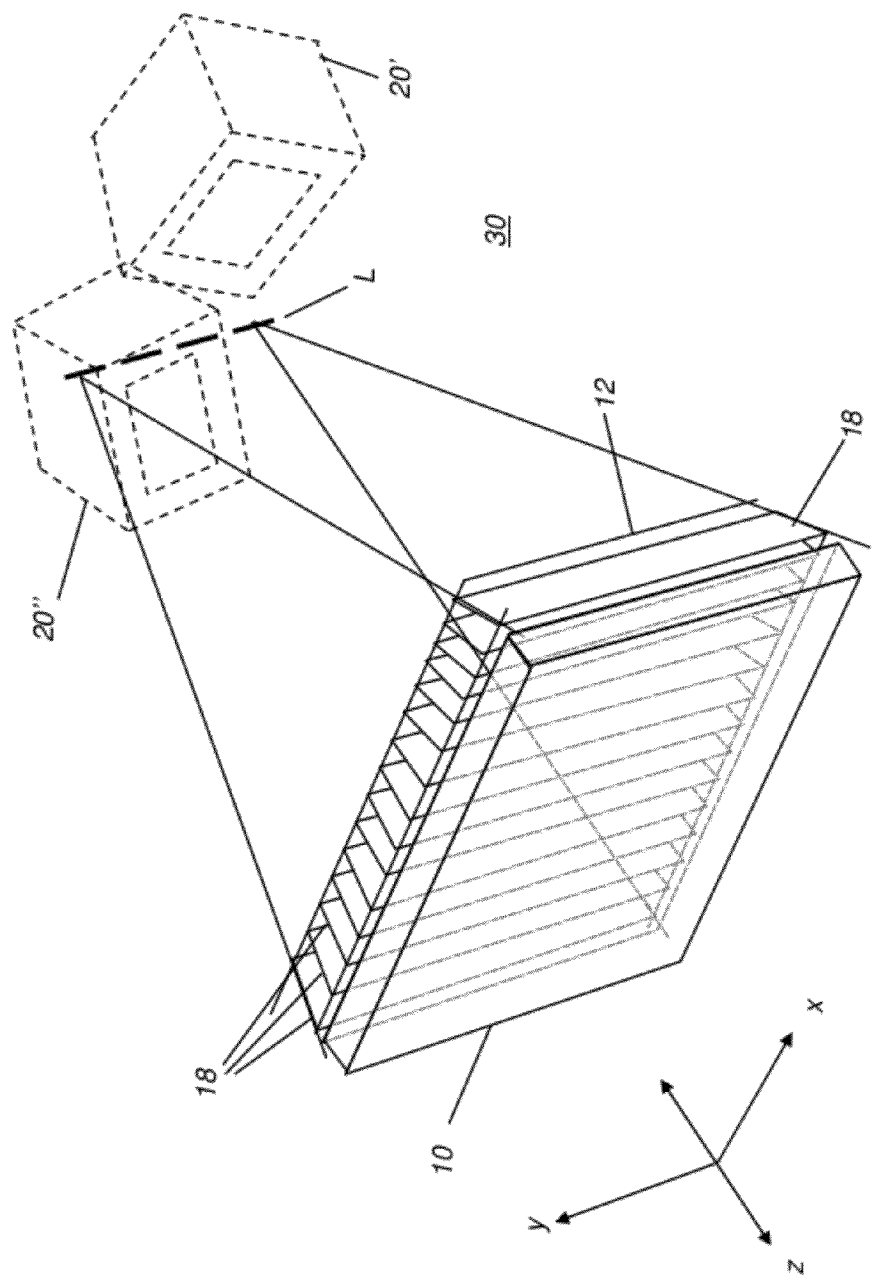
FIG. 2C is a perspective view showing exemplary out-of-alignment positioning.

FIG. 2C, by contrast, shows phantom outlines at 20' and 20" for poor positioning of radiation source 20. At positions 20' and 20" shown in phantom, the SID is almost acceptable; however, radiation source 20 is not centered near focal line L and its angular orientation is badly skewed. Alignment of the radiation source with the antiscatter grid would be poor at these and similar out-of-alignment positions, degrading image quality or, at worst, preventing a suitable diagnostic image from being obtained.

Figure 3A:
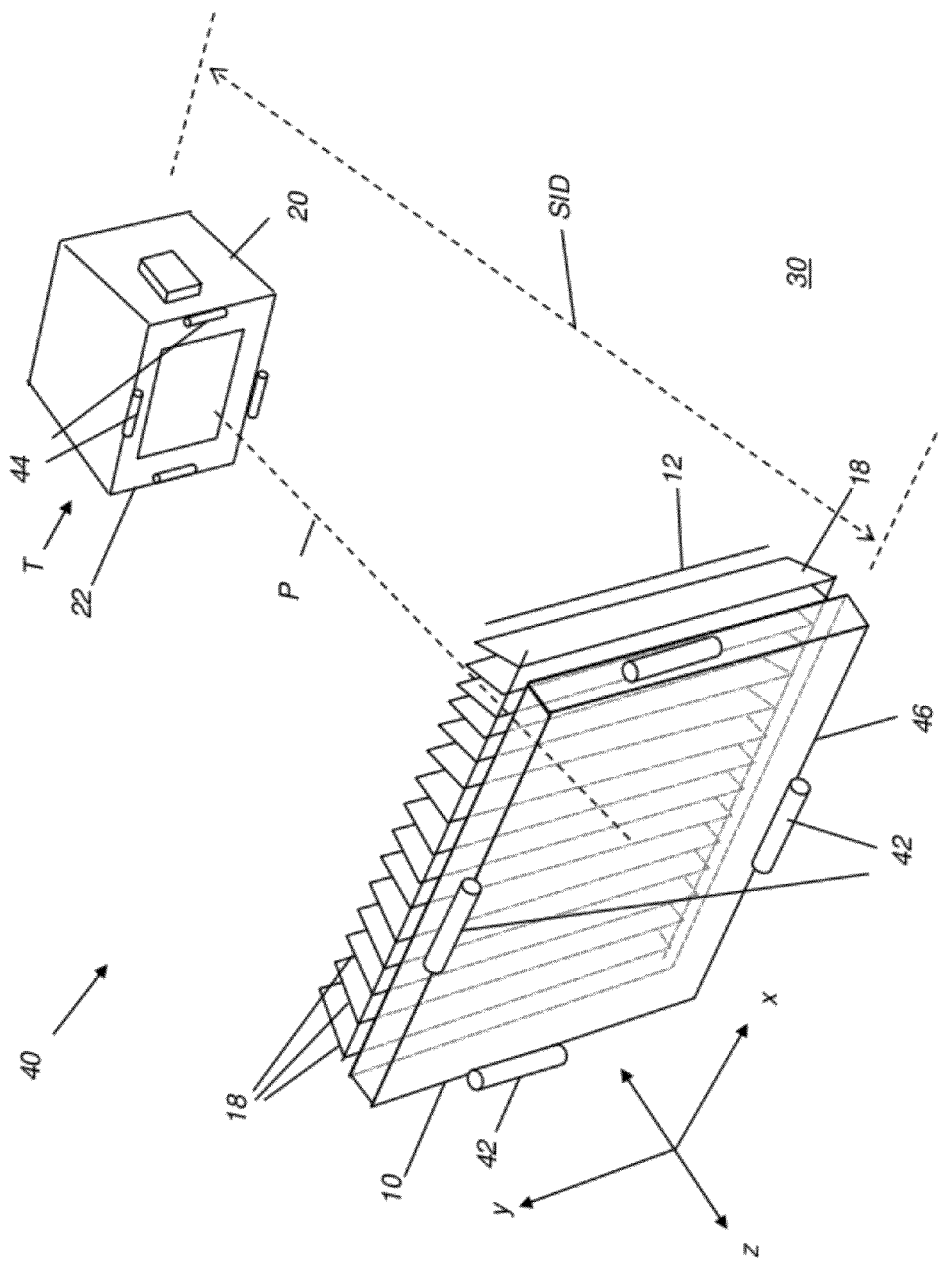
FIG. 3A is a perspective view showing the operation of one portion of an alignment apparatus in one embodiment.
Figure 3B:
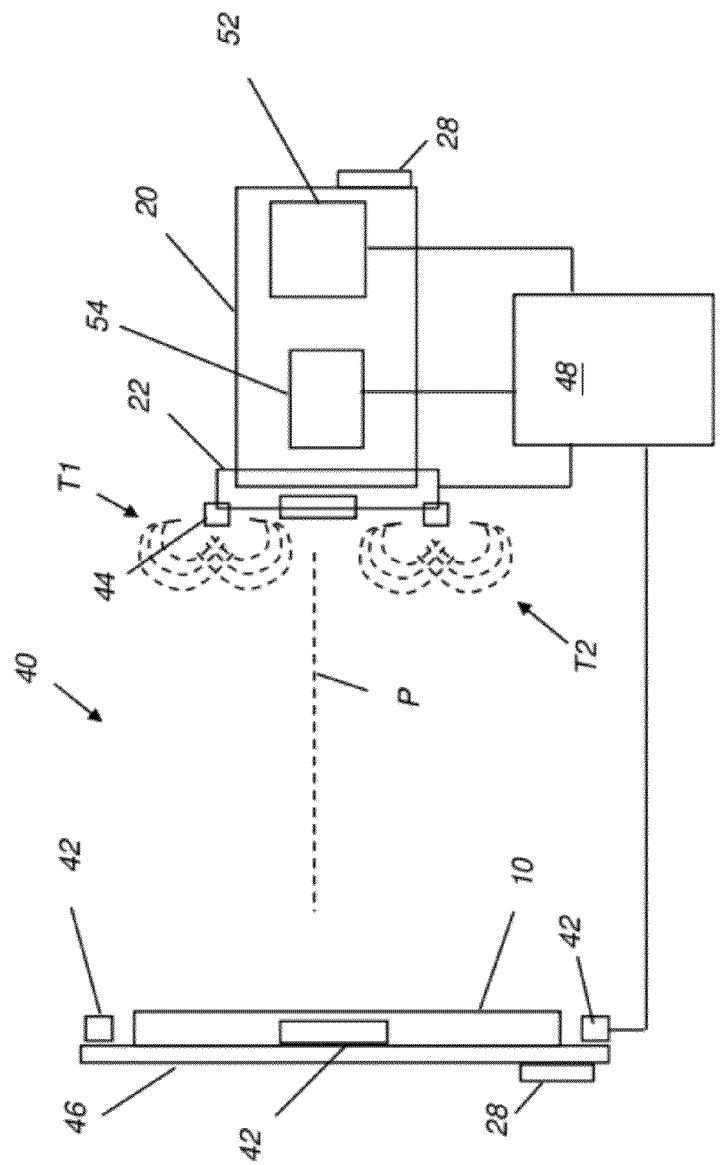
FIG. 3B is a side view block diagram that shows components used for achieving suitable tube to receiver/grid alignment according to an embodiment of the present invention.

The perspective view of FIG. 3A and side view of FIG. 3B show the use of an alignment sensing apparatus 40 that is energizable to sense the relative spatial relationship between radiation source 20 having a radiation path represented as path P and distributed about a central axis and imaging receiver 10 sensitive to radiant energy and positioned adjacent the subject for forming the radiographic image and to generate one or more output signals indicative of the relative spatial relationship, including alignment and distance. In the embodiment shown in FIGS. 3A and 3B, a holder 46 has one or more sensor elements 42 (e.g., electromagnetic coils) that are disposed outside the imaging area of the image receiver and that receive an electromagnetic field having time-varying vector directions or signal that is generated by a single emitter T or a pair of emitters T1 and T2, each emitter T, T1, or T2 comprising field generation elements 44, shown coupled to the radiation source 20, such as mounted near collimator 22 or generated by a motor that rotates a magnet or energized coil.

In one embodiment, the sensor elements 42 are not co-planar. In one embodiment, the field generation elements 44 are not co-planar.

Holder 46 also holds receiver 10. In an alternate embodiment, alignment sensing apparatus 40 components are built into receiver 10. In yet another alternate embodiment, the signal direction is reversed: signals are generated from one or more emitters T, coupled to receiver 10 on holder 46 and detected by sensor elements coupled with source 20. An additional sensor 28, such as an inclinometer, accelerometer, compass, gyroscopic, or other device for obtaining an angular measurement can be provided on either or both receiver 10 or radiation source 20. The one or more position-sensing signals from alignment sensing apparatus 40 go to a control logic processor 48 that provides the control logic for determining whether or not adjustment is needed and, optionally, for providing this information to a display apparatus 52, such as a display screen mounted on radiation source 20 as shown in FIG. 3B. In an alternate embodiment, an optional projector 54 is provided for projecting a display onto the patient or other subject indicating the status of the alignment and providing guidance on the particular adjustment that is needed.

Optional projector 54, shown mounted on the x-ray source 20 in FIG. 3B and following, may be a pico-projector, such as a Pico Projector Display from Microvision Inc., Redmond, Wash., USA, or a Micro Projector from AAXA Technologies, Inc., Santa Ana, Calif., for example. Image forming devices such as these are advantaged for a number of reasons, including small size, low weight, and low power requirements. These small-footprint projectors, currently used in cell-phone and other highly portable electronic devices, scan one or more low-power solid-state light sources, such as light-emitting diodes (LEDs) or lasers onto a display surface. This type of projector requires a small number of optical components for projection over a range of distances. The solid-state light source itself can typically be turned on and off rapidly as needed, so that power is consumed only for those image pixels that are projected. This allows the display device to operate at low power levels, so that battery power could be used for projector 54. Alternate embodiments use other types of electronic imaging projectors as image forming apparatus, such as those that employ a digital micromirror array such as the Digital Light Processor (DLP) from Texas Instruments, Inc.; an array of micro-electromechanical grating light valves, such as the Grating Light Valve (GLV) device from Silicon Light Machines, Inc.; or a liquid crystal device (LCD) including a Liquid Crystal on Silicon (LCOS) device. In an alternate embodiment, projector 54 is provided by a light source and a movable target, with a motor or other actuator that moves the target, where the target is positioned in the path of the light source for providing an image that shows the receiver location.

Figure 4:
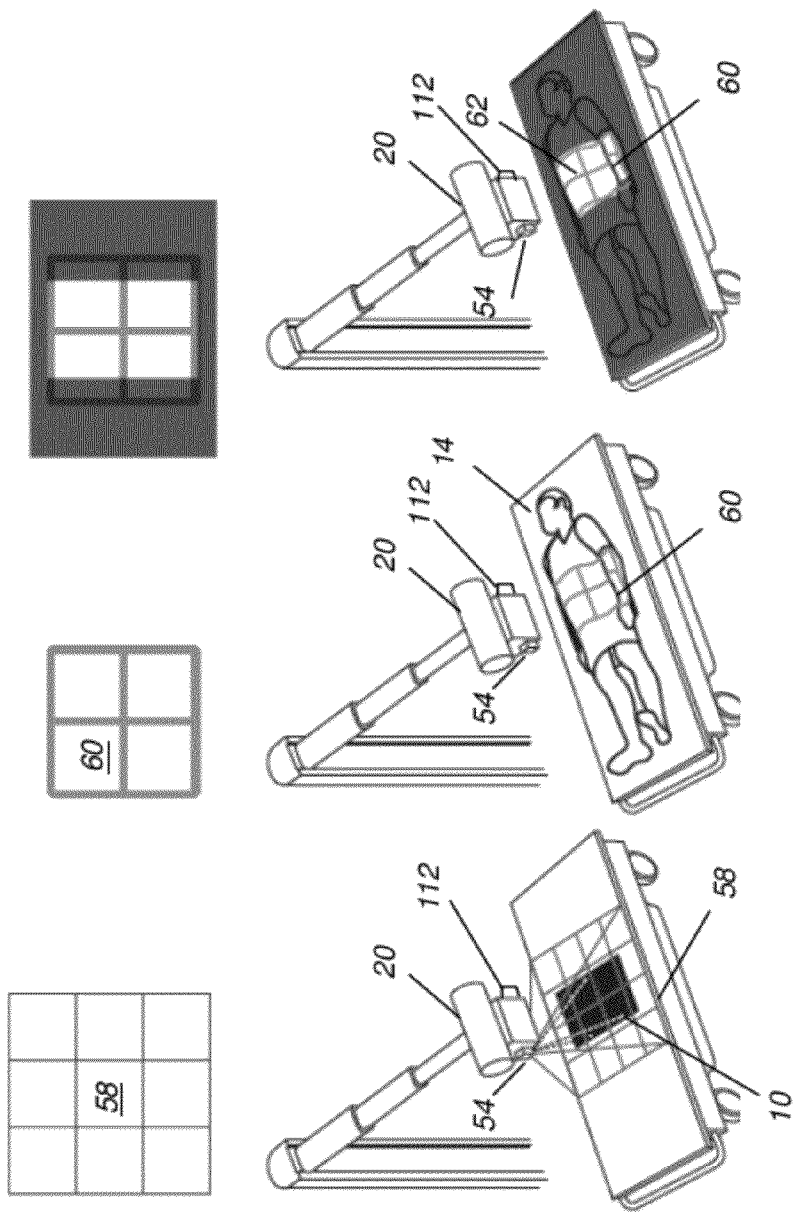
FIG. 4 is a perspective view that shows display of receiver position according to an embodiment of the present invention.

The perspective views of FIG. 4 show how optional projector 54 performs the display function according to one embodiment of the present invention. Projector 54 can project light to form images over an image field 58 that exceeds the area of receiver 10, as shown at left. When receiver 10 is located using alignment sensing apparatus 40, projector 54 displays a receiver pattern 60 on patient 14, wherein receiver pattern 60 indicates at least an outline showing the location of receiver 10 behind or underneath patient 14. At the right, the desired alignment is shown, wherein a collimator pattern 62, emitted from the collimator light source in the x-ray tube head, is aligned with receiver pattern 60. Notably, with this arrangement, projector 54 can project an image over an area that exceeds the size of receiver 10, enabling the outline of receiver 10 to be displayed prior to centering of the collimator and radiation path onto receiver 10.

Figure 5A:
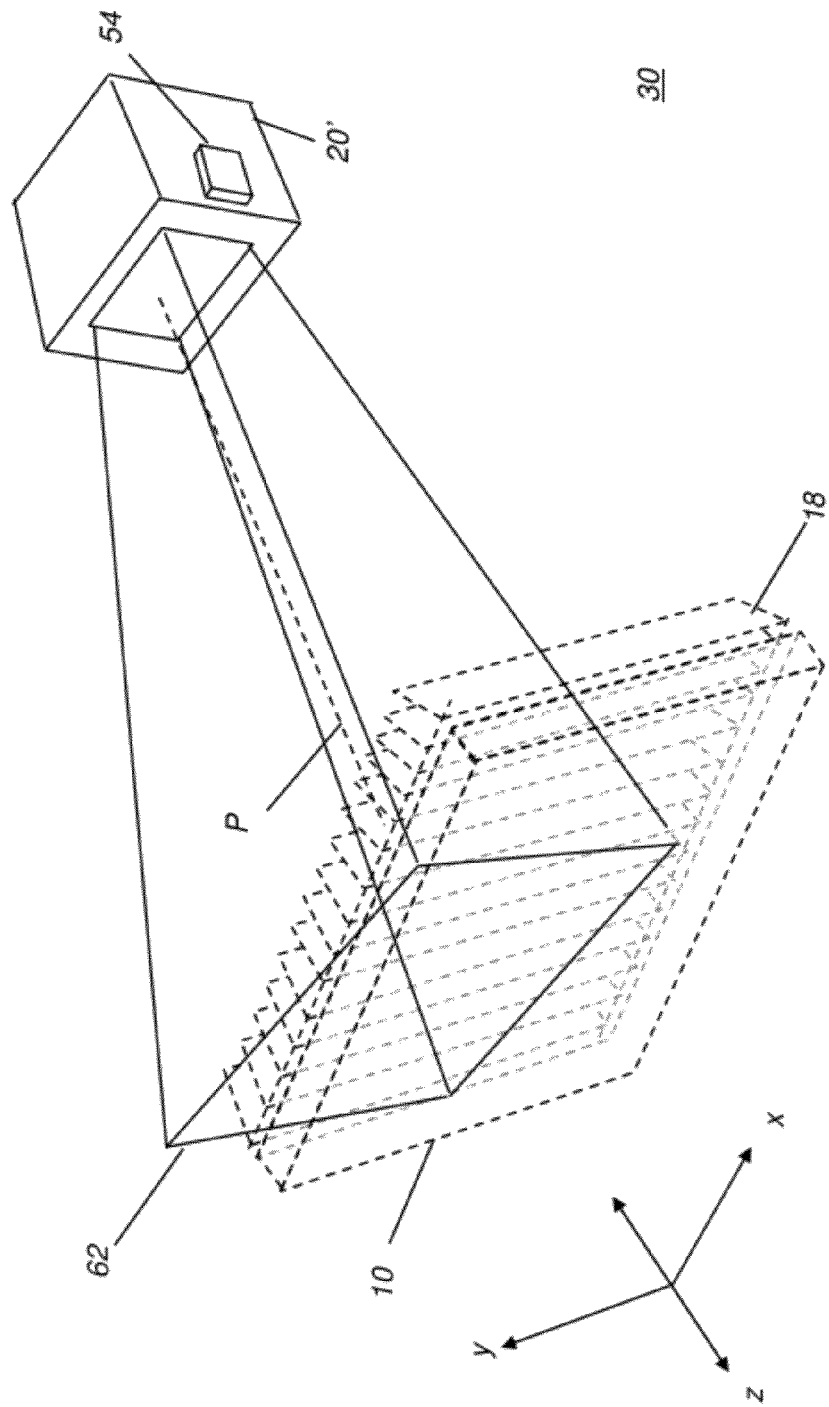
FIG. 5A shows display of a collimator pattern where the radiation source is poorly aligned to the receiver.
Figure 5B:
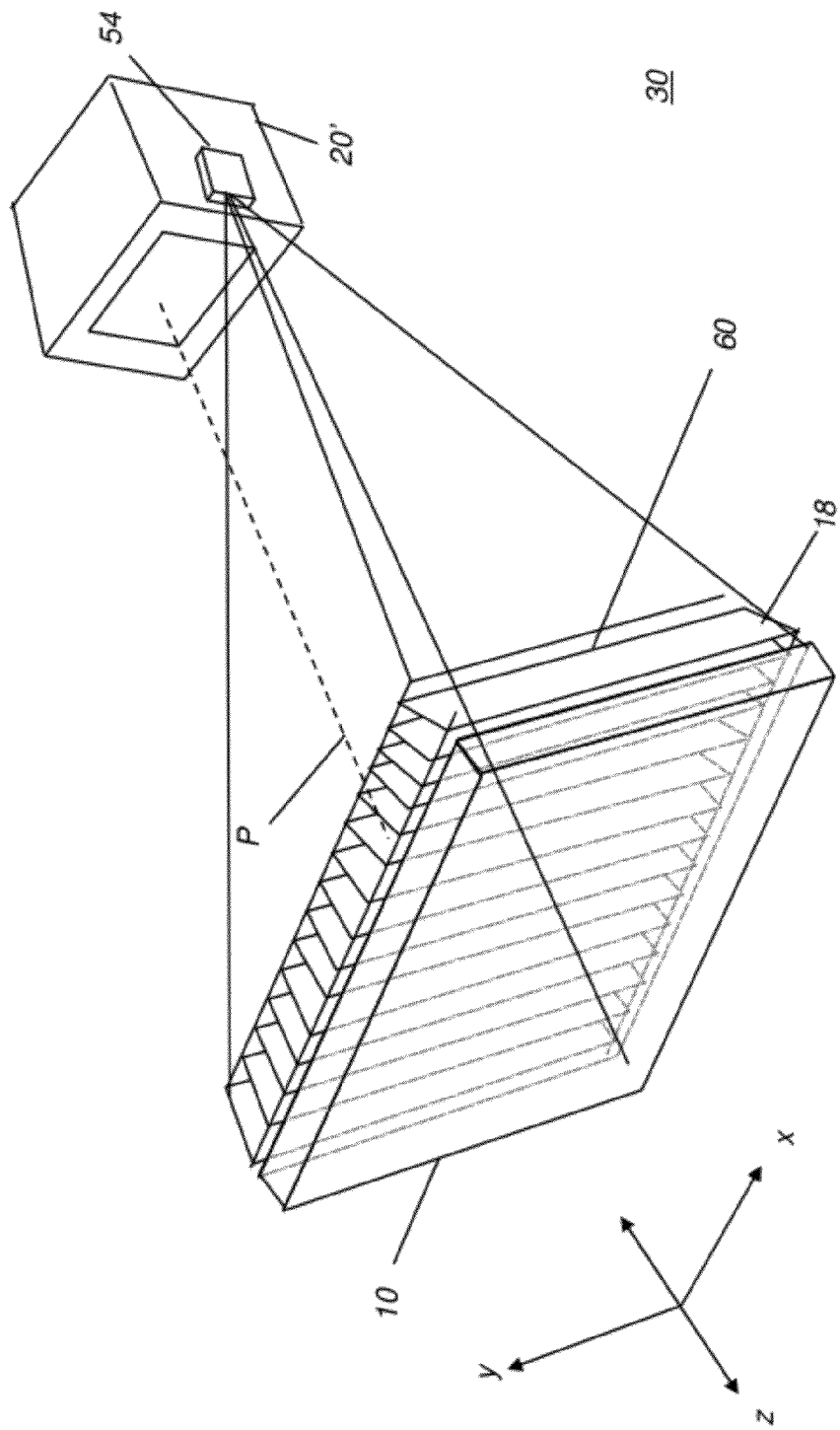
FIG. 5B shows display of a collimator pattern where the radiation source is well aligned to the receiver and anti-scatter grid.
Figure 5C:
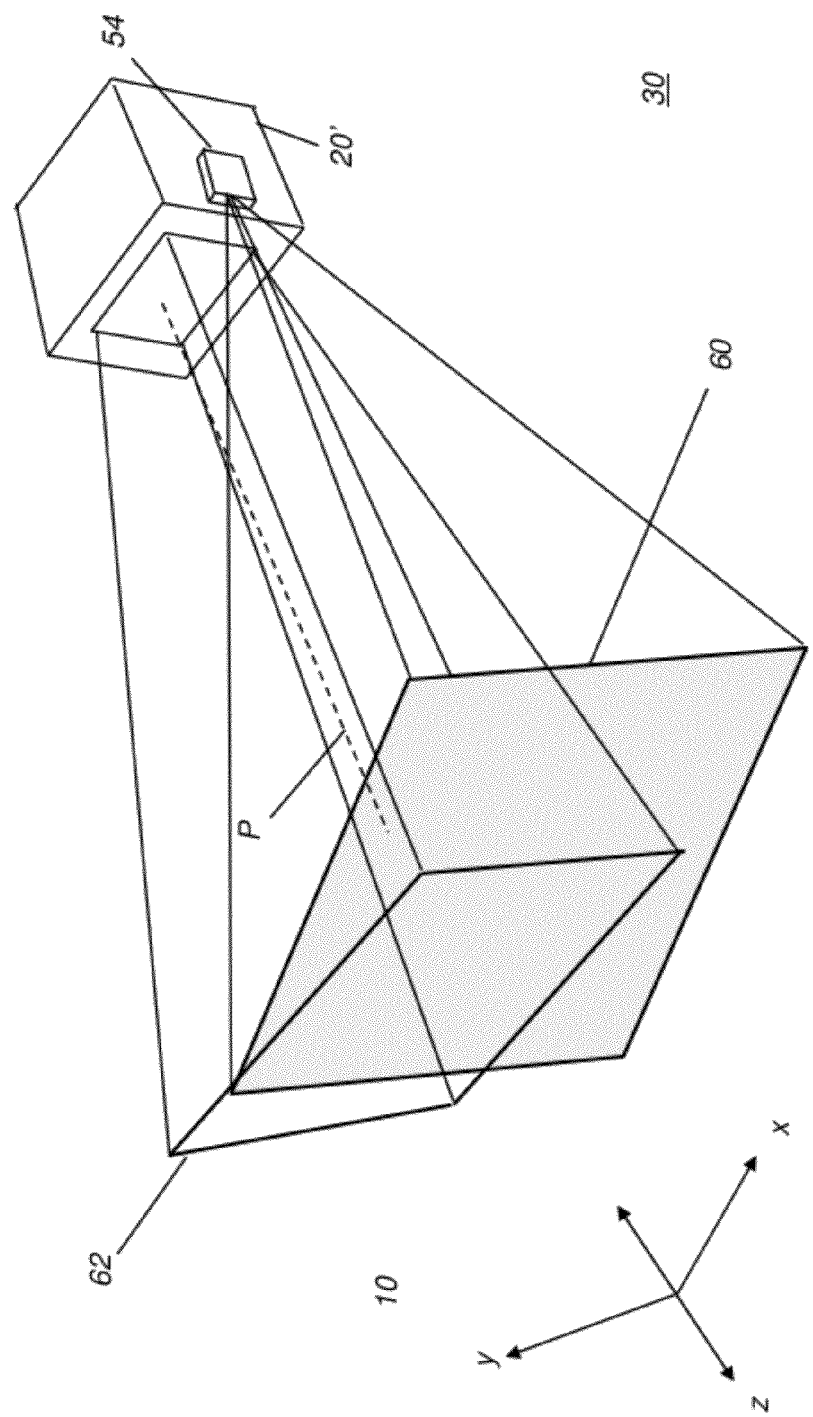
FIG. 5C shows display of a projected collimator pattern where the radiation source is poorly aligned to the receiver.
Figure 5D:
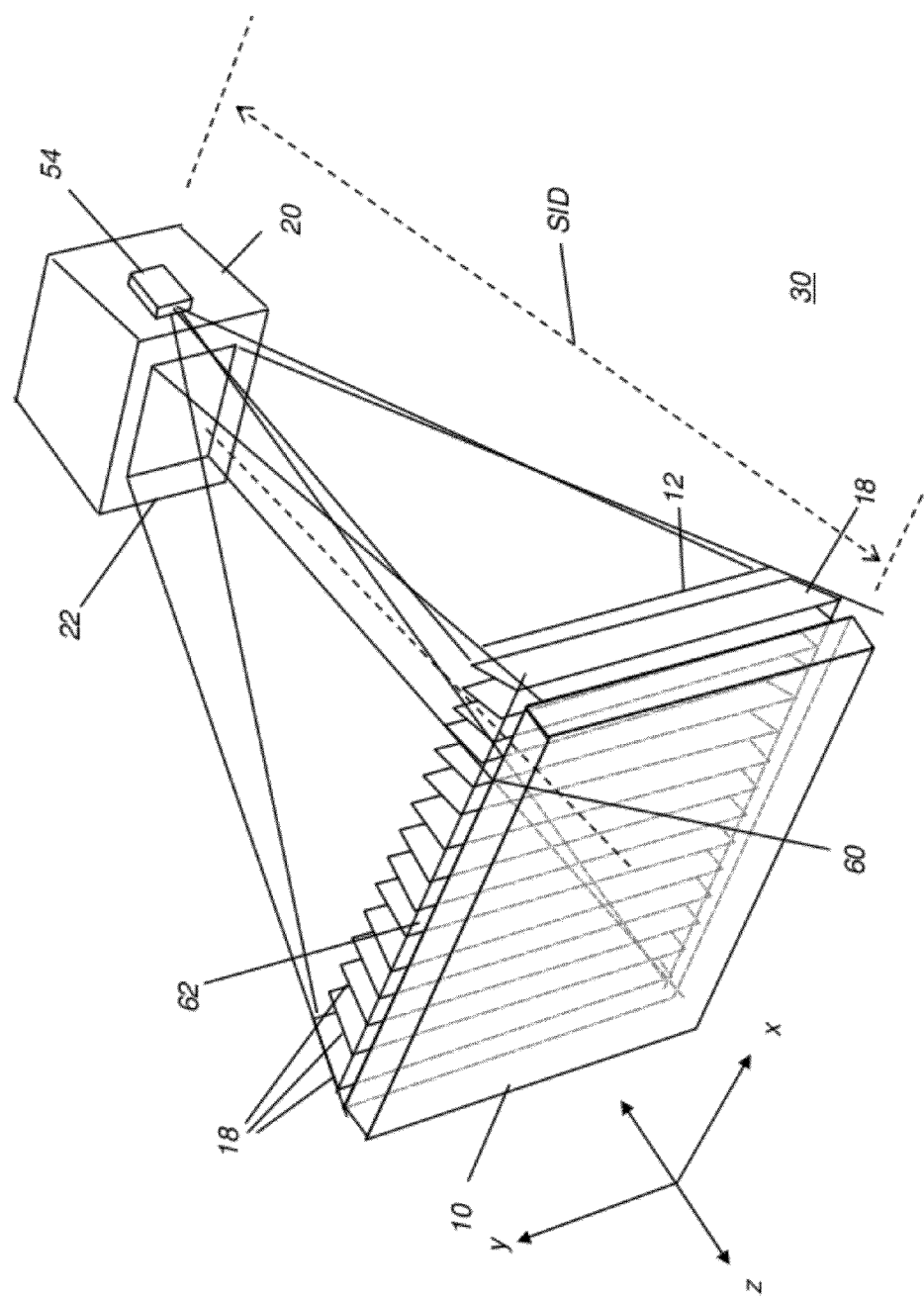
FIG. 5D shows display of a projected collimator pattern where the radiation source is well aligned to the receiver and grid.

The perspective view of FIG. 5A shows collimator pattern 62 that is displayed from radiation source 20 in a spatial arrangement wherein the radiation path of radiation source 20 (centered along axis P as described previously) is not aligned with receiver 10 or its grid 12. The perspective view of FIG. 5B shows projector 54 in display apparatus 50, projecting receiver pattern 60 directly at receiver 10. FIG. 5C shows the overlaid paths and mismatched patterns 60 and 62 that indicate poor alignment between radiation source 20 and receiver 10. The perspective view of FIG. 5D then shows correct alignment, wherein receiver pattern 60 and collimator pattern 62 are center-aligned and symmetrical. It can be observed that parallax problems between projector 54 and the collimator pattern 62 can be encountered when the SID is incorrect, with receiver 10 either too far or too near with respect to radiation source 20.

Figure 6B:
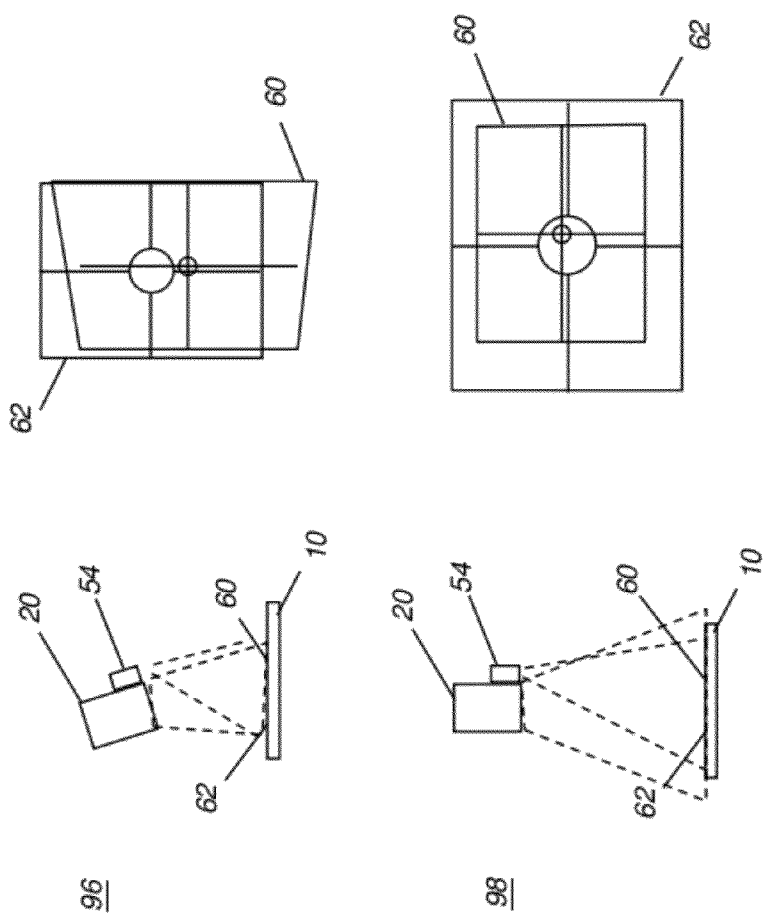

The positional relationship of displayed patterns from projector 54 and from the collimator light of the x-ray tube head can be used as indicators of alignment. By way of example, FIG. 6A shows how alignment of collimator pattern 62 from the collimator light with receiver pattern 60 from projector 54 indicates needed alignment adjustment of radiation source 20 with its receiver 10. The patterns shown at 60 and 62 are representative examples selected for illustration and can take any of a number of forms, including, but not limited to, crosshair patterns, including crosshair patterns with or without a central circle as shown in the example of FIGS. 6A and 6B. At a relative position 90, source 20 and receiver 10 are not aligned and respective patterns 62 and 60 indicate this misalignment. At a relative position 92, source 20 is closer to alignment with receiver 10, closer to centering than shown at position 90, and patterns 62 and 60 display as somewhat overlapping but are not centered with respect to each other. At a relative position 94, source 20 and receiver 10 are aligned and the displayed respective patterns 62 and 60 are overlaid to indicate this centering alignment. In addition, position 94, with both patterns 60 and 62 at the same size and over substantially the same area, also indicates that the collimator has been properly set to limit the radiation distribution and to reduce the likelihood of backscatter. Values 66 for SID and angle are also displayed by projector 54. In an alternate embodiment, a source-to-object distance (SOD) also displays. The projected values can be positioned within or outside receiver pattern 60. In alternate embodiments in which collimator blade position can be sensed, additional information on properly sizing and orienting the collimated light beam can also be provided in the display.

FIG. 6B shows other examples that represent poor relative positioning of source 20 and receiver 10. In a relative position 96, source 20 is nearly centered with respect to receiver 10, but the angle is skewed from normal. Receiver pattern 60 is accordingly non-rectangular, such as having a keystone pattern, for example, indicating the angular relationship of the radiation path from source 20 and receiver 10. In a relative position 98, source 20 is nearly centered with respect to receiver 10, but either the source-to-image distance (SID) is incorrect or, if correct, the collimator should be adjusted to reduce backscatter. In this case, the respective patterns 60 and 62 appear to be of different sizes to indicate the need for SID adjustment.

Where projection is used for display apparatus 50, in addition to the receiver 10 outline, information of various types can be displayed on or alongside the patient, for example, location of the receiver, location of automatic exposure control (AEC) device, grid information, actual and recommended SID, patient information, and some portion of the alignment information.

Display Screen 52 as Display Apparatus 50

Figure 7:
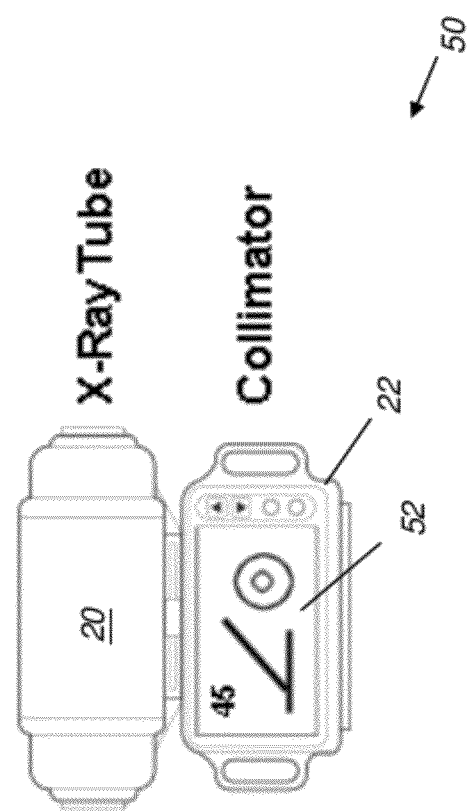
FIG. 7 is a plan view that shows the use of a display screen coupled to the collimator for displaying information indicative of the spatial relation between the radiation source and its receiver.

FIG. 7 shows display screen 52 that can supplement or substitute for projector 54 in an alternate embodiment of display apparatus 50. In one embodiment, display screen 52 is mounted near collimator 22 as shown, so that the operator can view displayed results while moving radiation source 20 into position. In alternate embodiments, the alignment utility may be provided on a removable or remote display screen or on display 610 (FIG. 1), the display console that is part of radiographic imaging apparatus 30 itself.

Figure 8A:
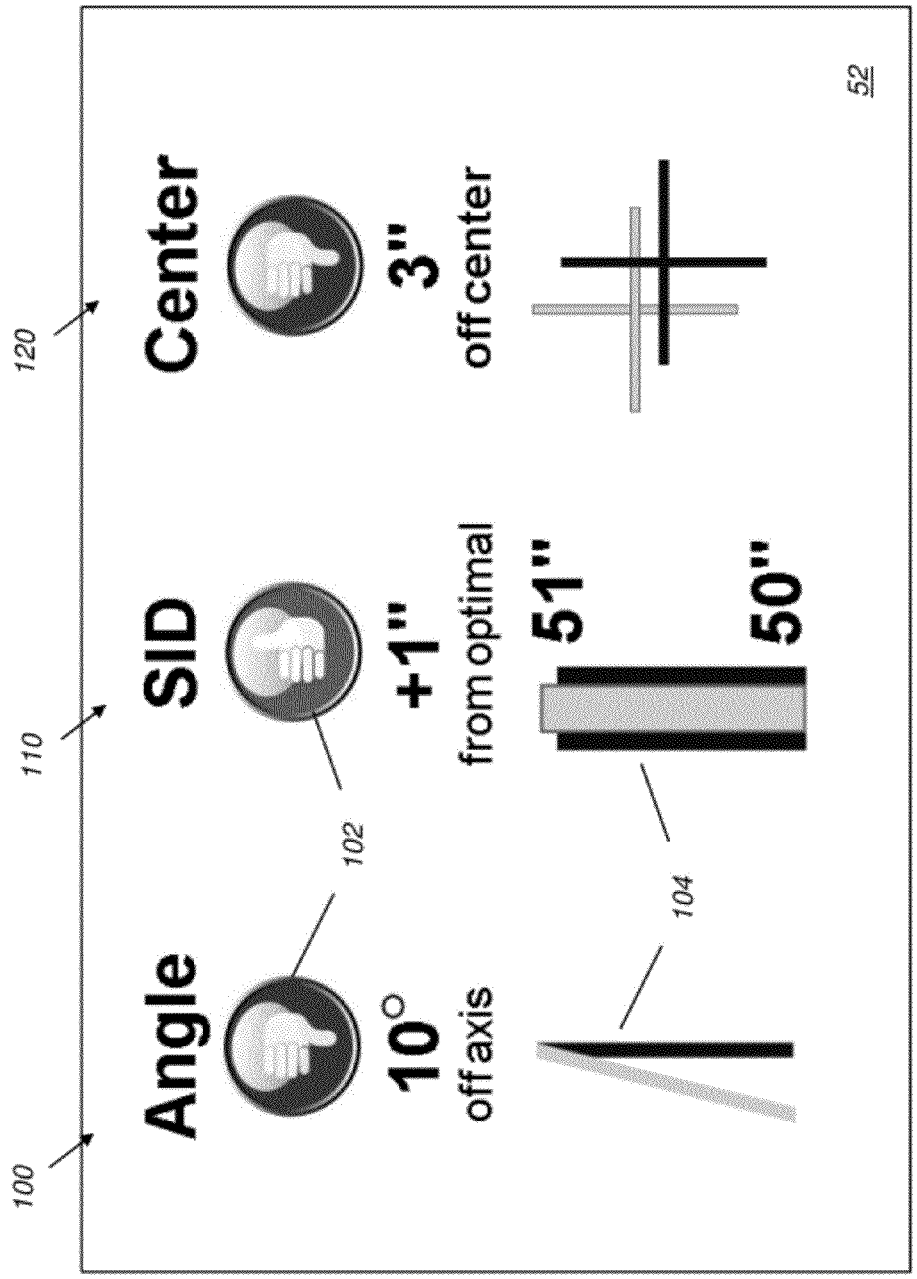
FIGS. 8A, 8B, and 8C show operator interface examples for use of a display screen as a display apparatus.
Figure 8B:
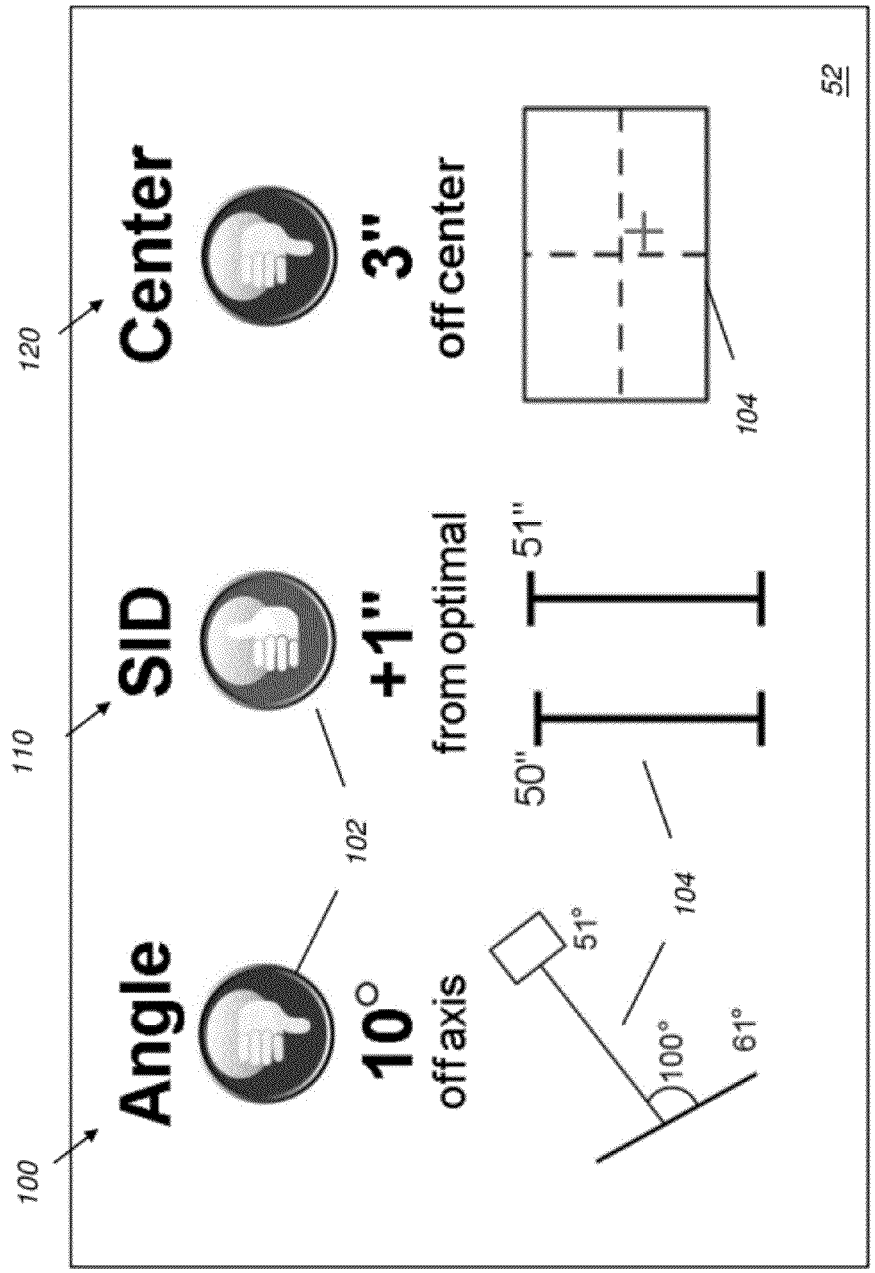
Figure 8C:
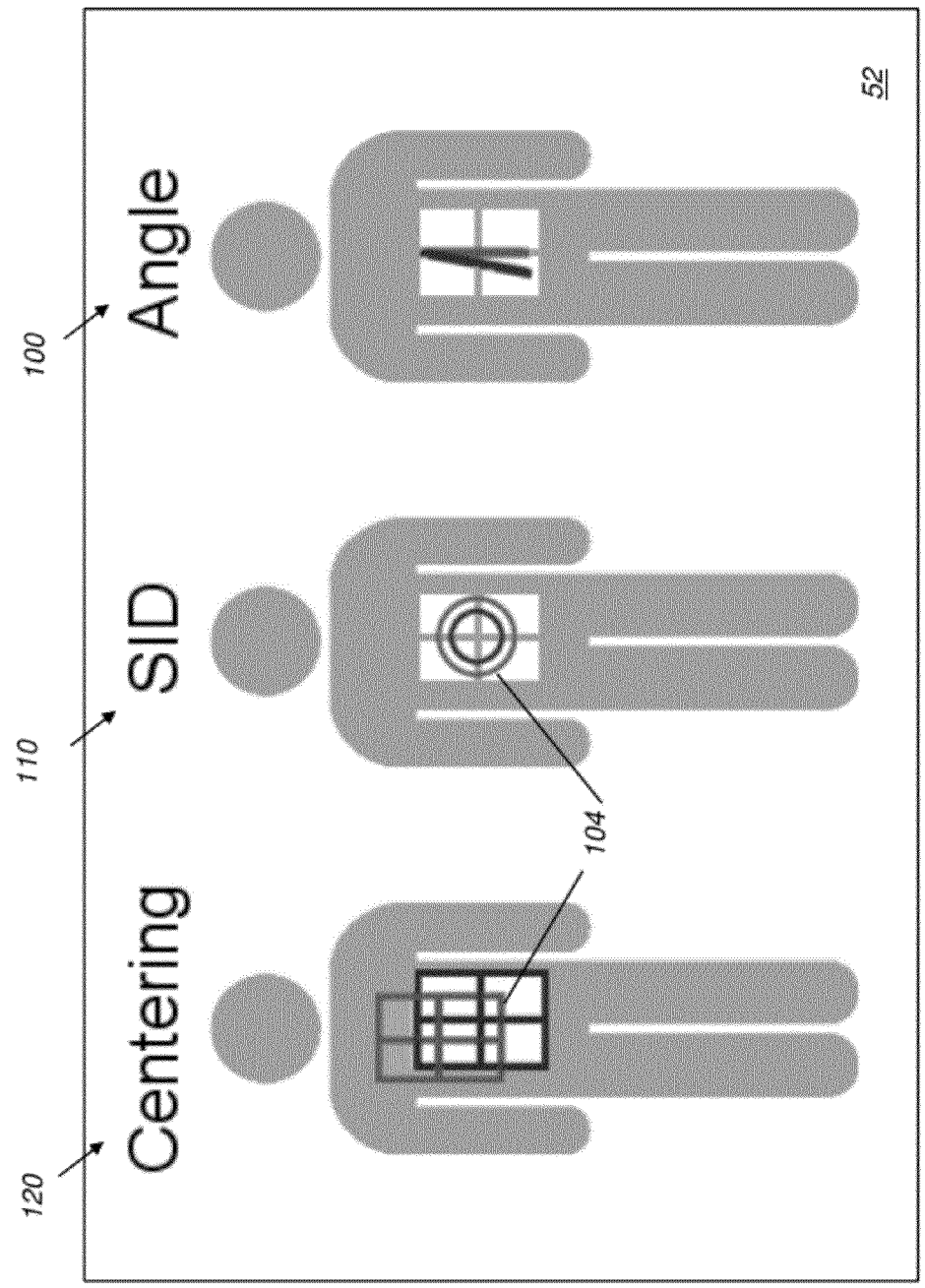

FIGS. 8A, 8B, and 8C show operator interface examples when using display screen 52 as display apparatus 50. Various graphical icons and images are used to symbolize the adjustments needed for proper centering, angulation, and SID. An angle adjust indicator 100 provides various graphical and measured data to help guide proper angular adjustment of the source 20 to receiver 10. Angular information displays one or more of the following:

(i) Receiver angle. An angular measurement relative to true horizontal can be obtained from the optional inclinometer or other sensor 28 (FIG. 3B) or from other alignment sensing apparatus 40 data.

(ii) Tube angle for radiation source 20. This angular measurement relative to true horizontal can similarly be calculated from inclinometer or other sensor 28 or other alignment sensing apparatus 40 data.

(iii) Receiver/grid to source 20 angle. This relative angular measurement between receiver 10 and source 20 can be obtained using measurements from one or more optional sensors 28 (FIG. 3B) or from other alignment sensing apparatus 40 data.

(iv) Intercept angle data for source-to-grid 12 alignment.

(v) Source to receiver angle relative to desired angle, calculated from alignment sensing apparatus 40 measurements. This includes adjustment for non-normal angles.

A SID indicator 110 lists not only the current SID value obtained from measured data, but, in the embodiment shown, also shows the amount of adjustment needed. A centering indicator 120 provides text and graphical information on centering error and needed adjustment direction. In FIG. 8B, centering indicator 120 includes a graphic element 104 that shows the portrait/landscape orientation of the receiver. Icons 102 use color, animation, including flashing or video clips, and symbols of different types to indicate the needed adjustment direction for the corresponding value. Graphic elements 104 are also provided to help visually indicate the adjustment needed. Graphic elements 104 can be any of a number of types of suitable element, including circles, bars, or other shapes. Color can be used to indicate correct angular, centering, or distance values, with differences in color indicating the recommended direction of needed change, if any, and color transitions indicating movement between positions. Various thresholds are used to determine how close an adjustment is to a desired setting.

Figure 9:
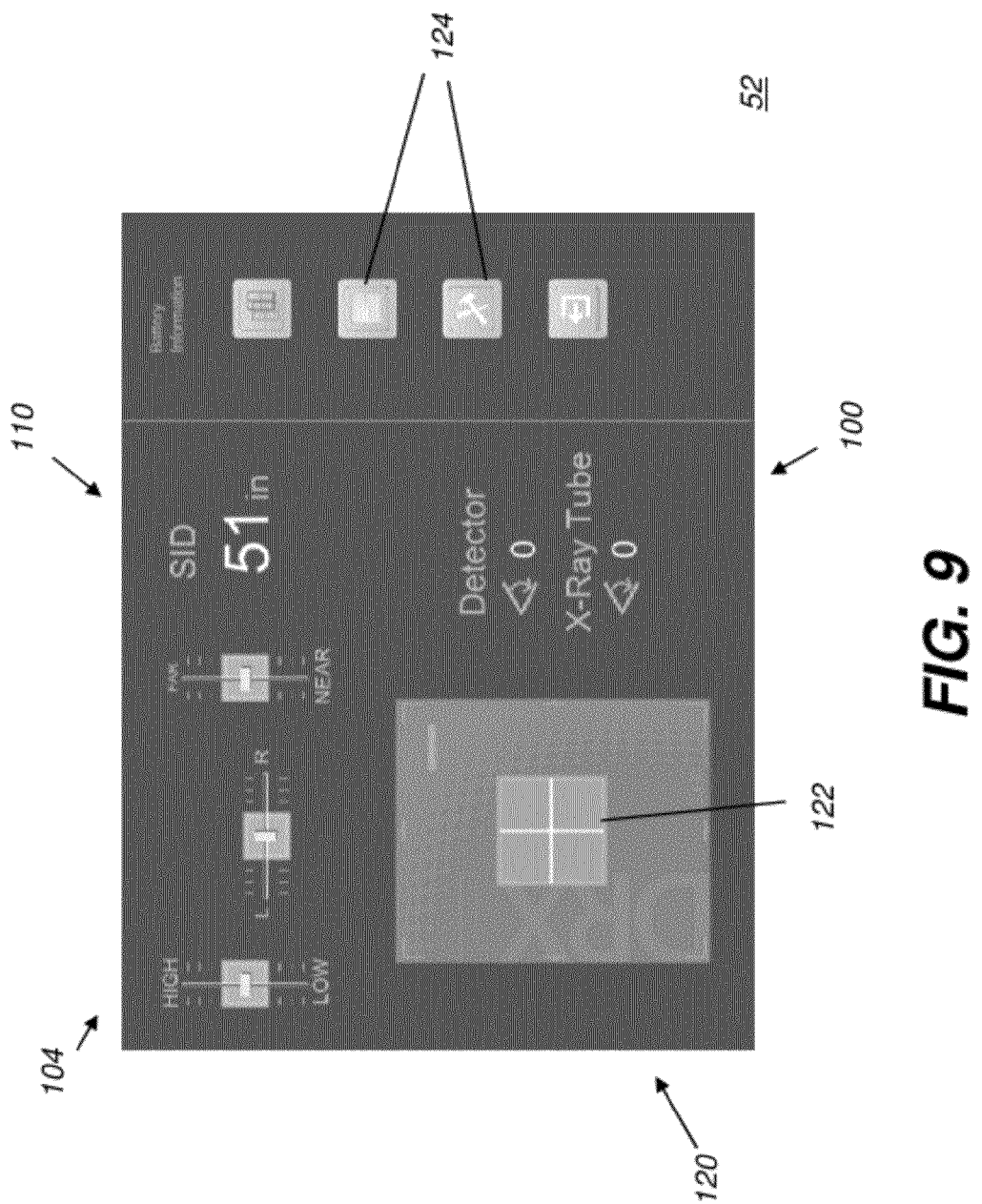
FIG. 9 shows an operator interface arrangement for the display screen in an alternate embodiment.

FIG. 9 shows a plan view of an alternate embodiment for the operator interface on display screen 52. SID indicator 110 lists the current SID value obtained from measured data. Here, graphic elements 104 include sliders that show the relative amount of adjustment that is needed for centering, distance, and angle. Centering of the slider indicates correct positioning. Angle adjust indicator 100 shows the measured angular values for the receiver or x-ray source relative to true horizontal or, optionally, relative to each other or to a preferred setting. In an optional embodiment, the difference between their relative angles is displayed. Centering indicator 120 shows an image or outline of receiver 10, such as at portrait or landscape orientation, with a superimposed icon 122 that shows the relative position and shape of the x-ray beam. Control buttons 124 provide useful utilities for improving alignment, obtaining information about the system or about system components, and other functions. In an alternate embodiment, one of the control buttons 124 is used to set up the view type for the upcoming radiographic image (such as, for example, an AP chest exam view type) and to indicate the type of grid used, if any. This setup can then cause specific SID and angle values to be assigned and displayed for the image.

Figure 10:
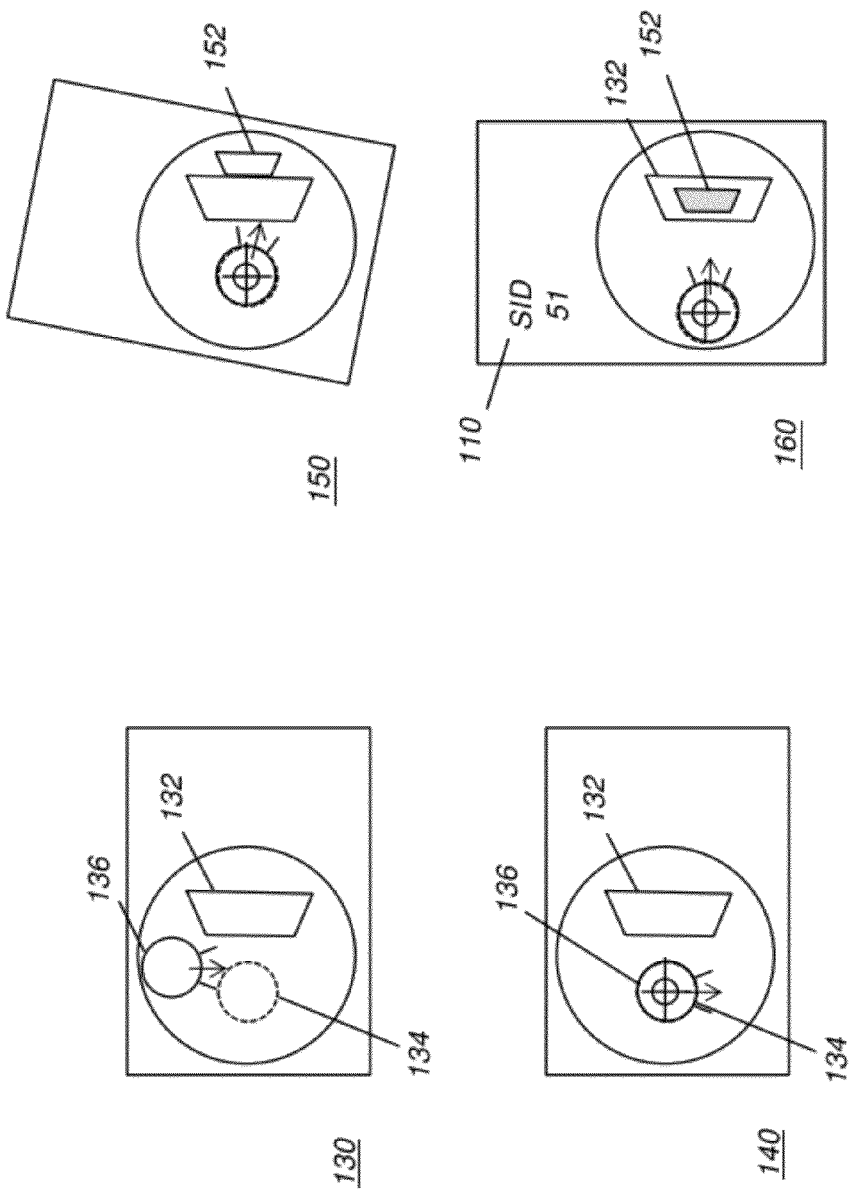
FIG. 10 shows a sequence of operator interface display screens for a display screen that is mounted near the collimator that changes orientation as the radiation source angle changes.

FIG. 10 shows a sequence of operator interface display screens for a display screen 52 that is mounted near collimator 22 and that changes orientation as radiation source 20 angle changes. At a position 130, a receiver icon 132 displays, along with a centering target icon 134 and a radiation source icon 136. At a position 140, centering is partially achieved, but the radiation source 20 must be redirected toward the receiver. At a position 150, radiation source 20 is being turned and the screen display dynamically re-orients itself to represent positions of components with receiver icon 132 and icons 134 and 136. A SID icon 152 graphically shows that radiation source distance to the receiver must be adjusted. SID icon 152 changes position as the SID changes. At a position 160, proper centering, angle, and SID are obtained. The SID value displays as shown at SID indicator 110.

In one embodiment, sensors are also able to indicate whether or not grid 12 is used and, if so, the type of grid 12 that is being used. The system can then display information such as Transverse or Longitudinal grid type; Grid ratio, for example: 6:1, 8:1, 10:1; optimal SID (or SID range) for the grid being used; and indication or message to use the correct grid type (transversal or longitudinal) based on detected rotation of the receiver. If the patient is not lying flat, the system can determine this through the grid's inclinometer data, and can also determine this condition using other sensor data. The system can also provide a warning message related to grid cutoff, a condition that occurs when the angle of the radiation path is excessively skewed to one side or the other of the grid, causing the grid elements to block a substantial amount of radiation. When the presence or absence of a grid is determined, system logic can automatically select the correct view for the exam or change the existing view to a different one. For example, the system can switch from a non-grid view to a grid view. This new view may have a different name, different exposure parameters or techniques, and different image processing parameters. In an alternate embodiment of the present invention, the image type or view is determined and one or more appropriate settings for centering, angle, and SID are automatically assigned based on the view type. The view can be set up by the operator, such as using display screen 52 and may specify the type of grid used. Alternately, the view can be determined from measured data, such as inclinometer readings, for example.

Alignment Apparatus

As noted previously, alignment is of particular value when a grid 12 (FIG. 2A, for example) is used with the imaging receiver. Alignment of the source to the grid helps to improve the obtained image by reducing scatter.

Figure 11:
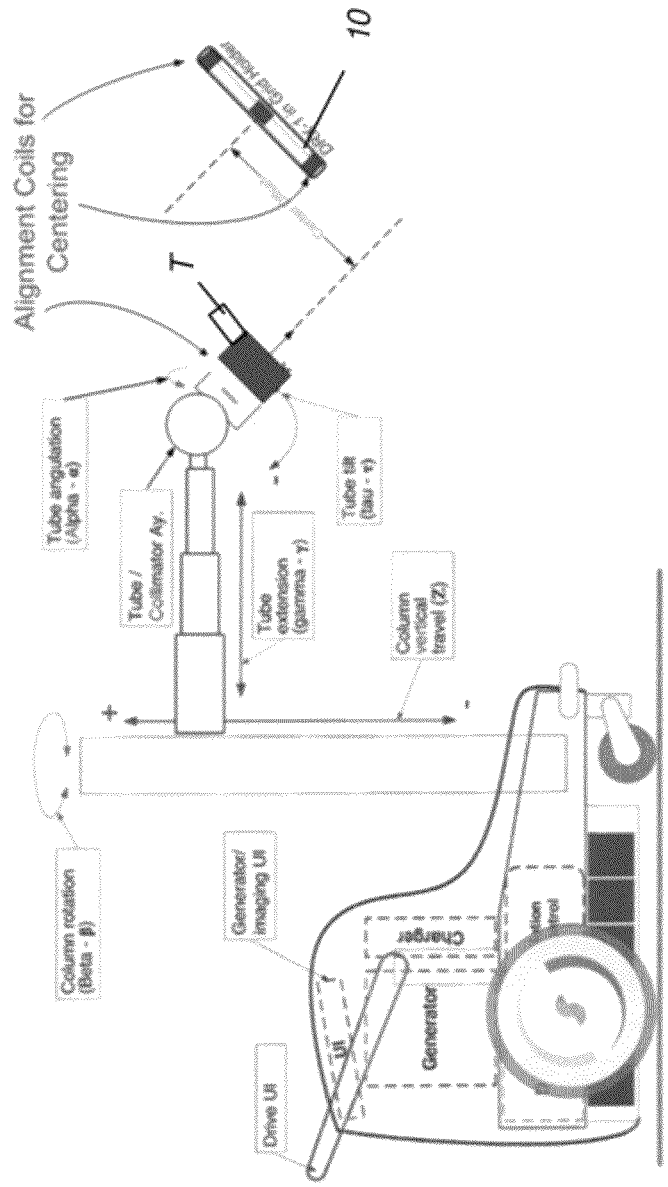
FIG. 11 is a schematic view showing a radiographic imaging apparatus that uses an alignment apparatus according to an embodiment of the present invention.

The schematic view of FIG. 11 shows radiographic imaging apparatus 30 using alignment apparatus 40 and labels the two translation and three rotational stages plus collimator rotation needed for alignment. In the embodiment of FIG. 11, a single emitter apparatus T is used for alignment. Embodiments with a pair of emitter apparatus T1 and T2 are also used.

Embodiments of the present invention provide positional information for source-to-detector alignment using emitter apparatus T that generates a magnetic field with a predetermined position field pattern relative to the mounting arrangement used for the emitter components and with continuously varying or time-varying vector direction and comparing signals sensed from the varying magnetic field by a set of sensors that are arranged at different positions. The predetermined position field pattern that is emitted can be the same pattern under any imaging conditions and does not vary in position relative to the position of the image receiver, but has the same position relative to the emitter circuitry and is dependent on the spatial position in which emitter T apparatus components 44 are mounted. For example, where a motor is used to generate the field pattern, the same rotated field pattern is used each time, as determined by the position of the rotated field generation element 44 and the motor axis. Where separate sine and cosine coils generate the field pattern as part of emitter apparatus T, this pattern is in fixed position relative to these components and this position does not change. These same components can also be used to provide the synchronization signal needed for using the detected sensor signals to determine relative position.

Figure 12A:
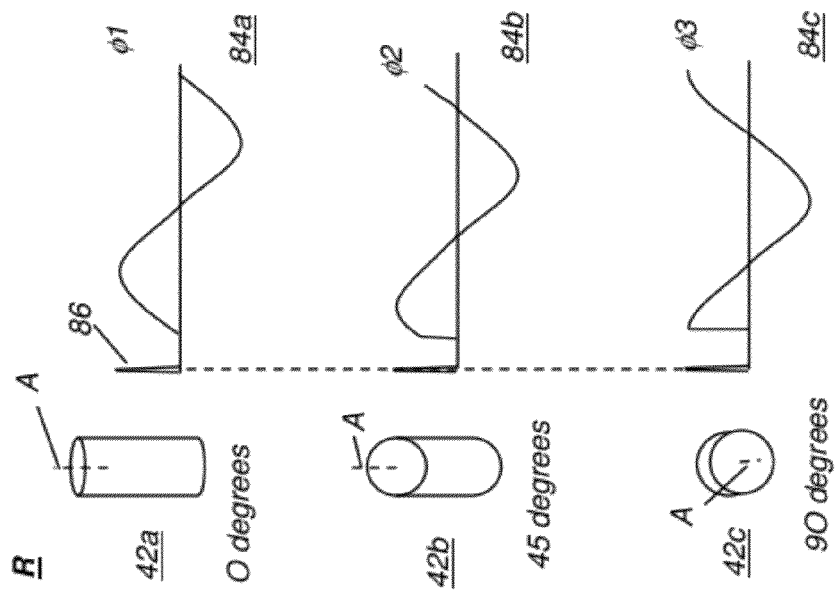
Figure 12A:
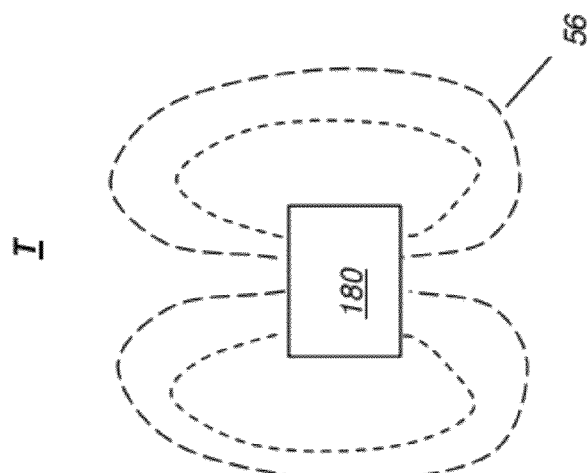

The schematic block diagram of FIG. 12A shows how this alignment mechanism sensing can operate. At an emitter apparatus T, a signal generator 180 generates, about itself, a time-varying magnetic field that has a periodic varying magnetic vector pattern, with a fixed field position pattern 56, at a predetermined frequency. At a sensing apparatus R, sensor elements 42a, 42b, and 42c are spread apart and at different angles with respect to the generated field. Each of sensor elements 42a, 42b, and 42c obtains a corresponding signal 84a, 84b, and 84c respectively. Signal amplitude at each sensor at any instance in time is indicative of the distance between emitter T and the sensor element and is also a factor of the direction of the sensor's highest sensitivity relative to the direction of the magnetic field vector. Where sensor elements 42a, 42b, and 42c are coils, for example, the direction of the sensor's highest sensitivity relates to the axis of symmetry A of the core of the coil.

As shown in FIG. 12A, signals 84a, 84b, and 84c from sensor elements 42a, 42b, and 42c are shifted in phase φ1, φ2, and φ3 from each other due to their relative angles with respect to the time varying magnetic field vector. A synchronization or sync signal 86 is generated from the emitter and is used to relate timing of the sensor signals to the orientation of the magnetic field vector in the emitter's frame of reference. This combination of sync signal timing with phase and amplitude information from each sensor element provides information useful for obtaining the relative positions of x-ray source and detector.

Emitter T can generate the magnetic field with time-varying vector direction in a number of ways. Where rotary motion is provided, a single coil or other field generating element can be used. FIG. 12B shows front and side views of an embodiment of signal generator 180 in emitter T with a motor 88 that spins a magnet 72 in order to generate the time-varying magnetic vector pattern that is needed. In one embodiment, magnet 72 is a permanent magnet. In an alternate embodiment, magnet 72 is a coil having a direct current (DC) drive.

Magnet 72 can also be a coil that is driven by an alternating current (AC) signal. In such an embodiment, the AC signal acts as a type of carrier signal, with the time varying vector direction change provided by the rotation from motor 88. Each sensor sees an amplitude modulation of the carrier signal over time, according to the sensor's direction of highest sensitivity relative to the rotational angle of the motor. Advantageously, using the AC signal allows tuning of the sensor elements in sensing apparatus R to have a higher gain at the frequency of the AC signal. This can provide an improved signal to noise ratio. In general, a carrier signal is at a frequency higher than the frequency of the magnetic field in space with time-varying vector directions that is generated by the emitter apparatus.

The time-varying magnetic field can also be formed using signal generator 180 that comprises two or more stationary coils or other emitters that do not require rotation but that cooperate to emit a magnetic field vector that is time-varying and can be detected by sensor elements. The time-varying magnetic field is generated by modulating the magnitudes of the field from each coil, with respect to time, in a synchronized manner. FIG. 12C shows front and side views of an alternate embodiment for signal generator 180 in emitter T, using two coils 182*a* and 182*b* disposed orthogonally or with some other angular difference between them. Coils 182*a* and 182*b* can be in different planes, as shown in FIG. 12C.

There are six degrees of freedom (DOF) for consideration in source-detector positioning. To determine relative positioning, at least six independent position-related measurements are required. A solution can be found using at least one emitter T generating a time varying magnetic field vector, with three or more sensor elements at the sensing apparatus R. This arrangement can provide both a phase and magnitude measurement on each of the three sensing elements to provide the required six independent measurements to solve for six unknown degrees of freedom. Alternately, two emitters T1 and T2, each generating time varying magnetic field vectors, could be used, with two or more sensor elements at sensing apparatus R in order to get sufficient independent measurements to determine the source-detector positioning.

Sync signal 86 is provided by emitter T or, alternately, from some external timing mechanism. This signal can be provided in the magnetic field itself, such as by generating a short pulse magnetic signal or other timed signal or may be provided using a wired signal connection, such as a signal from control logic processor 48, for example.

Figure 13:
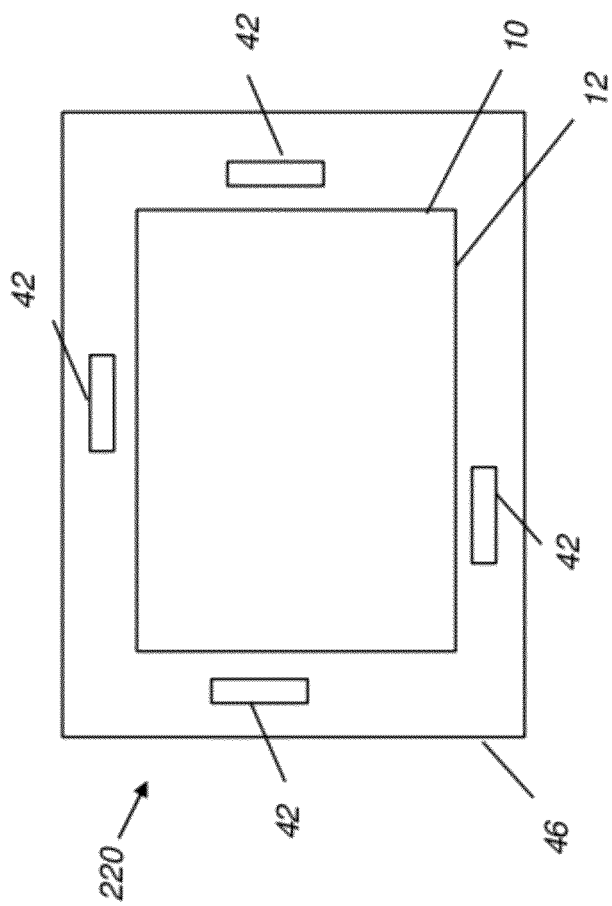
FIG. 13 is a plan view showing a receiver and anti-scatter grid in a holder that provides sensing elements that form a sensor apparatus.

The plan view of FIG. 13 shows receiver 10 and its grid 12 seated within holder 46. Using the principle described in FIGS. 12A, 12B, and 12C for emitted and sensed magnetic fields, the direction of the generated magnetic field is sensed using the apparatus of FIG. 13 and used to indicate the relative alignment of each sensor element 42 to emitter apparatus 44. The receiver signals are synchronously measured from each of the sensor elements 42 and recorded. Sensor elements in the sensing apparatus are spatially separated to take advantage of signal triangulation. Sensor elements 42 can be peripheral to image receiver 10 and lie outside the imaging area of the image receiver 10, as shown in FIG. 13. Where sensor elements 42 are coils, their axes of symmetry, (the same as the axis of symmetry of each core element of the coil), lie in planes that are generally parallel to the planar surface of receiver 10. Sensed magnitude and phase information is evaluated mathematically to derive the relative position and orientation between emitters and sensor elements. Associated as part of each sensor element 42, described subsequently in the present disclosure, is supporting signal amplification and measurement circuitry, along with components for maintaining signal communication with control logic processor 48 (FIG. 3B).

The use of stationary emitter coils, as described with reference to FIG. 12C, is advantaged by eliminating the need for motor or other actuator with moving parts to provide the time-varying magnetic field by rotating the coil or other field generation element 44. As was shown in FIGS. 3A and 3B, for a stationary emitter T, there can be at least two field generation elements 44 on radiation source 20, with the two field generation elements 44 that form each emitter T typically disposed orthogonally with respect to each other. Field generation elements can alternately be at any known relative orientation and spacing apart from each other. Field generation elements 44 are typically paired coils.

It should be noted that additional field generation elements 44 and additional sensor elements 42 can be used to advantage for position detection, using strategies such as disposing sensor elements 42 at other angles. According to one embodiment herein, three or more sensor elements 42 are provided, with adjacent elements rotated at 45 degree increments with respect to each other. This allows additional signal information to be available, so that more accurate positional and orientation measurement can be obtained. Further, the relative positions of sensor and field generation elements 42 and 44 could be reversed from that shown, so that field generation elements 44 of emitter apparatus T are on holder 46 and sensor elements 42 disposed on radiation source 20. To help reduce induced surface current effects, coils for generation and sensing are aligned substantially parallel to nearby metal surface structures, such as parallel to the metallic case of the DR receiver 10 or parallel to collimator features, for example. For a sensor coil, substantially parallel alignment means alignment of the core axis to within about 10 degrees of parallel, preferably within no more than about 2 degrees from parallel. For other types of sensor devices, substantially parallel alignment means alignment of the highest axis of sensitivity to within about 10 degrees of parallel or less.

Figure 14A:
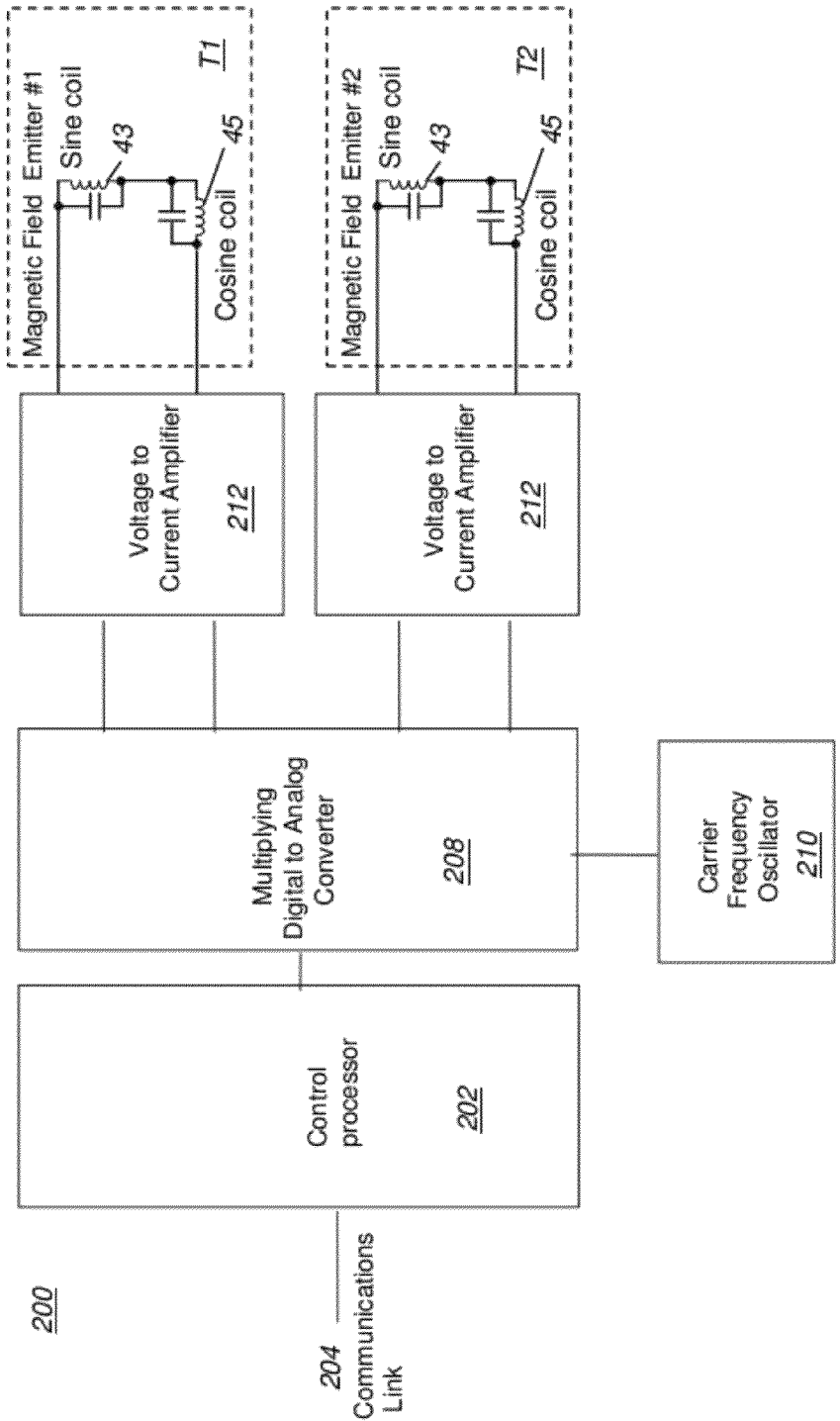
FIG. 14A is a schematic block diagram that shows components of an emitter apparatus.

The schematic block diagram of FIG. 14A shows an emitter circuit 200 for generating and emitting the time varying magnetic field from a pair of emitter apparatus T1 and T2 according to an embodiment of the present invention. Each emitter apparatus T1 and T2, in the embodiment shown in FIG. 14A can modulate separate field generation elements, which can include a sine coil 43 and a cosine coil 45. A control processor 202, in signal communication over a communications link 204 with other control logic, such as control logic processor 48 (FIG. 3B), coordinates control of this modulation with a digital-to-analog (D/A) converter 208 and oscillator 210 to provide signals to appropriate voltage-to-current amplifiers 212 that drive the coils of field generation elements 44. Control processor 202 provides a control circuit that can alternately energize each emitter apparatus T1, T2 during a discrete time interval, so that both pairs of field generation elements, sine and cosine coils 43 and 45 respectively, are not emitting a magnetic field at the same time. An optional oscillator 210 provides a carrier frequency that is amplitude-modulated within a waveform envelope, such as a sinusoidal envelope, according to one embodiment of the present invention. The respective coils in sensor and emitter apparatus T elements are tuned to the carrier frequency. Selection of a suitable carrier frequency can be based on a number of factors, including power and distance considerations, relative degree of penetration through the patient, interference with nearby equipment, signal-to-noise ratio, and other factors. Consistent with an embodiment of the present invention, a carrier frequency ranging from several kHz to several MHz can be used. In general, the carrier signal is at a frequency higher than the frequency of the magnetic field with time-varying vector directions generated from the emitter apparatus.

To take advantage of the relationship of phase to position described with reference to FIGS. 12A-12C, the emitted magnetic field is a modulated signal that varies over time, such as a sinusoidal or other repeatable or periodic signal. This field is typically emitted from one emitter apparatus T1, T2 at a time and repeats as often as is necessary to help establish the spatial relationship between the x-ray source and receiver. In the embodiment of FIG. 14A, for example, each emitter apparatus T1, T2 can emit its magnetic field over a separate time interval. Emission by the first emitter apparatus T1 terminates, or is in the process of being terminated, before emission by the second emitter apparatus T2 begins, so that their respective time intervals for magnetic field generation are at least substantially non-overlapping. Sine coil 43 and cosine coil 45 can be spatially separated by a variable distance, such as in the same plane, or may be disposed in different planes. Spatial separation of sine coil 43 and cosine coil 45 can help to improve signal processing accuracy, as is useful for triangulation, for example.

Figure 14B:
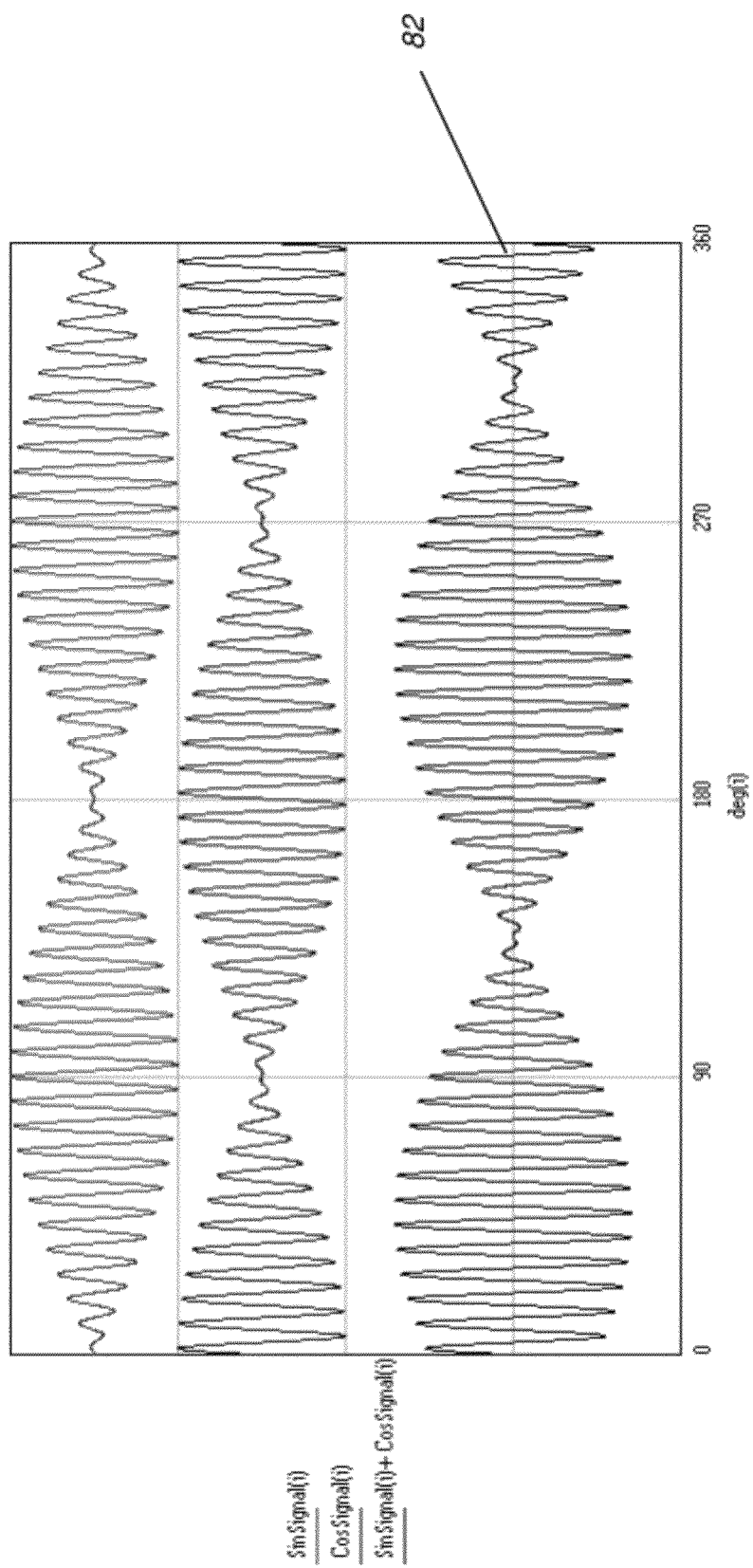
FIG. 14B shows waveforms generated by the emitter apparatus of FIG. 14A.
Figure 14C:
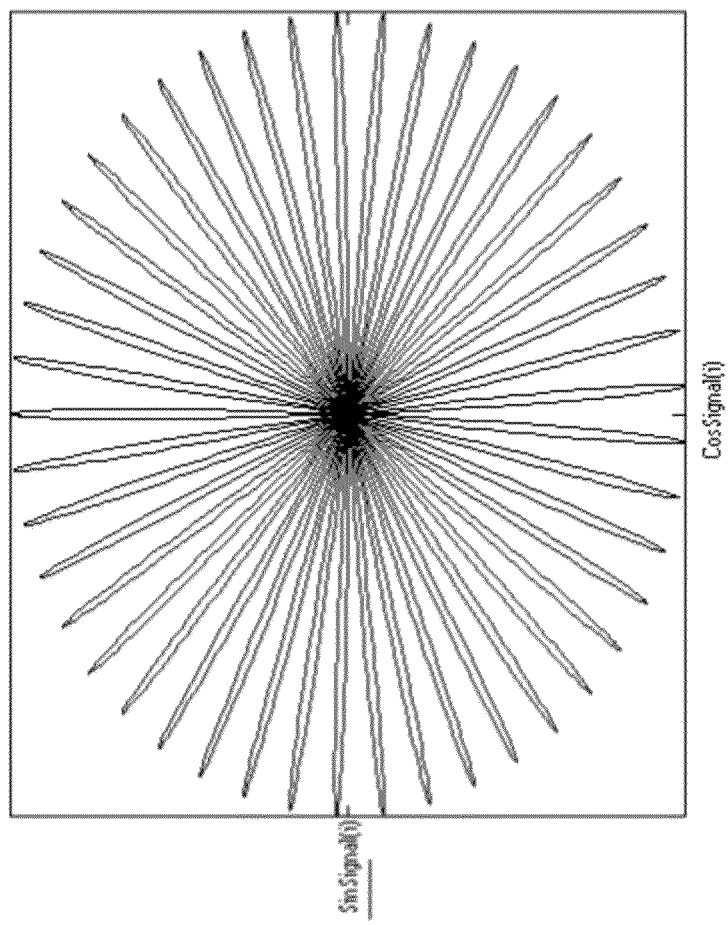
FIG. 14C shows the pattern of the rotating magnetic field vector from orthogonally disposed sine and cosine coils, as modulated in the emitter apparatus.

Use of a carrier signal is optional, but has advantages for detection of the time-varying magnetic field over a distance and in a noisy environment. Sensor elements 42 can be tuned to the carrier frequency, to improve the signal-to-noise ratio. The wave forms shown in FIG. 14B show the modulated carrier frequency in a sinusoidal envelope, as emitted signal 82, detected at sensor elements 42, formed by summing signals from paired sine and cosine coils. By way of exemplary schematic illustration and example, FIG. 14C shows the pattern of the rotating magnetic field vector from orthogonally disposed sine and cosine coils, as modulated in the emitter apparatus.

Figure 15A:
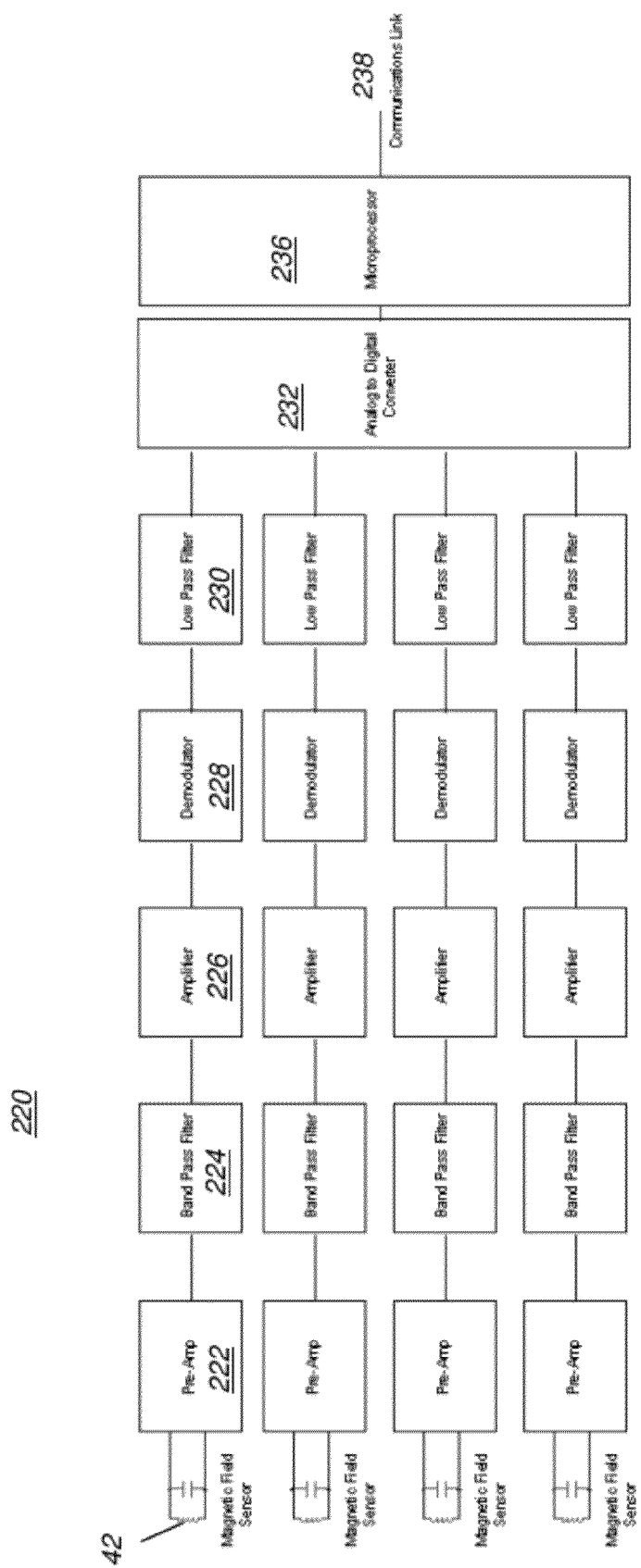
FIG. 15A is a schematic block diagram that shows components of a sensor apparatus.

The schematic block diagram of FIG. 15A shows a sensing apparatus 220 for obtaining and conditioning the emitted signal from emitter circuit 200. Each sensor element 42 can be a coil according to one embodiment of the present invention. Other embodiments employ some other device as sensor element 42, such as a Hall-effect sensing device, a magneto-resistive sensor, a Giant magneto-resistive (GMR) sensor, or Flux Gate sensor, for example. In an embodiment that uses a coil, the coil of each sensor element 42 can provide its signal to a pre-amplifier 222 and a band-pass filter 224 for noise removal. The signal can then be processed by an amplifier 226 and a demodulator 228. The de-modulated signal can be provided through a low-pass filter 230 to an analog-to-digital (A/D) converter 232. A control processor or other signal generation circuit 236, in signal communication over a communications link 238 with other control logic such as control logic processor 48 (FIG. 3B), is then energizable to generate an output signal, such as an output data signal that is indicative of the position and orientation of the sensing apparatus relative to the emitter apparatus, as well as the distance between the sensing and emitter apparatus. The function of signal generation circuit 236 can be performed by a dedicated microprocessor, as shown in FIG. 15A, or by some other circuit, such as an analog circuit, for example. Other components for indicating device orientation, such as an accelerometer, for example, can also be in signal communication with signal generation circuit 236.

As noted previously, emitter circuit 200 can be coupled to the x-ray source 20, such as installed at collimator 22, with corresponding sensing apparatus 220 as part of holder 46. In an alternate embodiment, the reverse arrangement can be used, with emitter circuit 200 coupled to receiver 10 and installed at holder 46 and sensing apparatus 220 coupled to x-ray source 20.

Figure 15B:
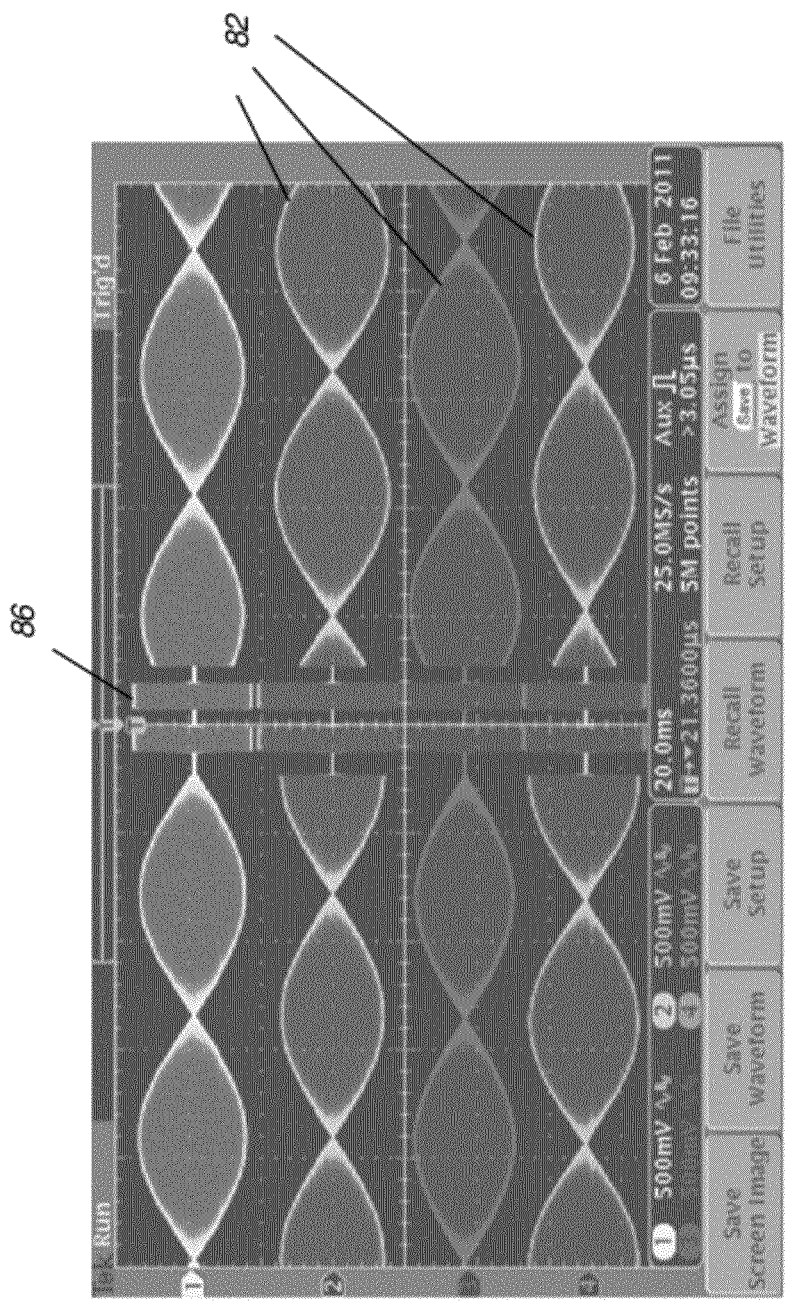
FIG. 15B shows waveforms acquired by the sensor apparatus of FIG. 15A.
Figure 15C:
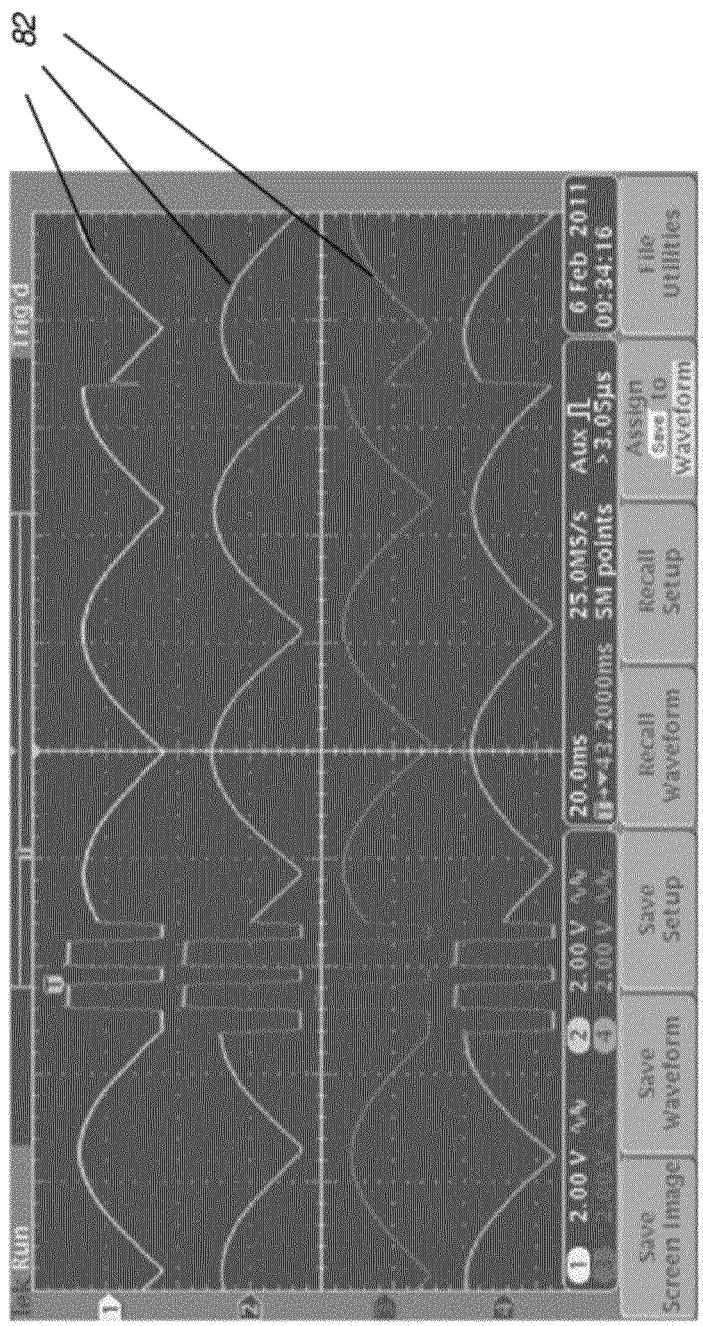
FIG. 15C shows the demodulated and filtered waveforms of FIG. 15B, processed by the sensor apparatus.

FIG. 15B shows exemplary received waveforms from sensing apparatus 220 for each coil of a set of sensor elements 42. The left half of this figure shows waveforms relating to the signal from emitter T1; the right half shows waveforms from emitter T2. Each row is the signal for one sensor element 42 coil. As can be seen from this figure, each sensor signal can have a different magnitude and phase for the same generated time-varying magnetic field, wherein the magnitude and phase depend on relative sensor position and orientation. Synch signal 86 can also be detected, as shown. FIG. 15C shows exemplary demodulated waveforms after processing through the circuitry of FIG. 15A.

Operation Sequence for Alignment

Figure 16A:
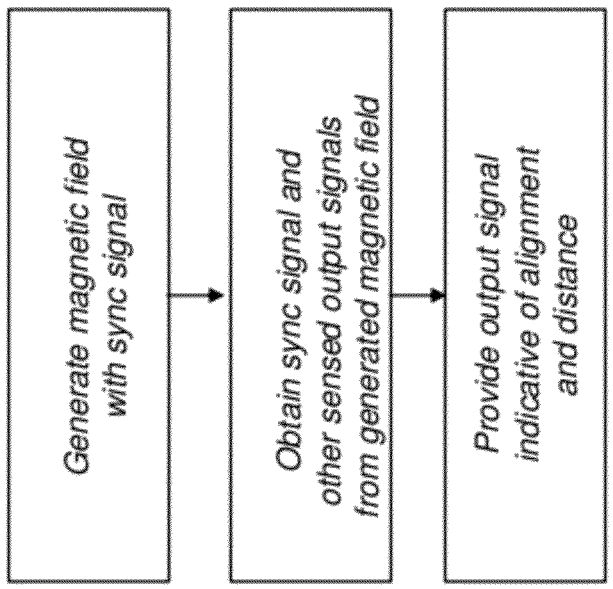
FIG. 16A is a logic flow diagram that lists basic steps for alignment according to an embodiment of the present invention.

The logic flow diagram of FIG. 16A lists basic steps for alignment according to certain exemplary embodiments. In a signal generation step 250, one or more magnetic fields with predetermined field pattern and time-varying vector direction can be generated from emitter apparatus T or, alternately, from emitter apparatus T1 and T2. A sync signal can also be generated as part of field generation. A signal sensing step 260 obtains sensed output signals from the generated magnetic field from a sensing apparatus that is coupled to the image receiver. The sensing apparatus has three or more sensor elements, wherein at least two of the sensor elements are arranged at different angles relative to each other and can be disposed outside the imaging area of the image receiver, as described previously. In an output signal step 270, an output signal is provided. This signal is indicative of an alignment adjustment, according to the amplitude and phase of the obtained sensed output signals relative to the synchronization signal. Subsequent exemplary descriptions provide additional detail related to this process.

Figure 16B:
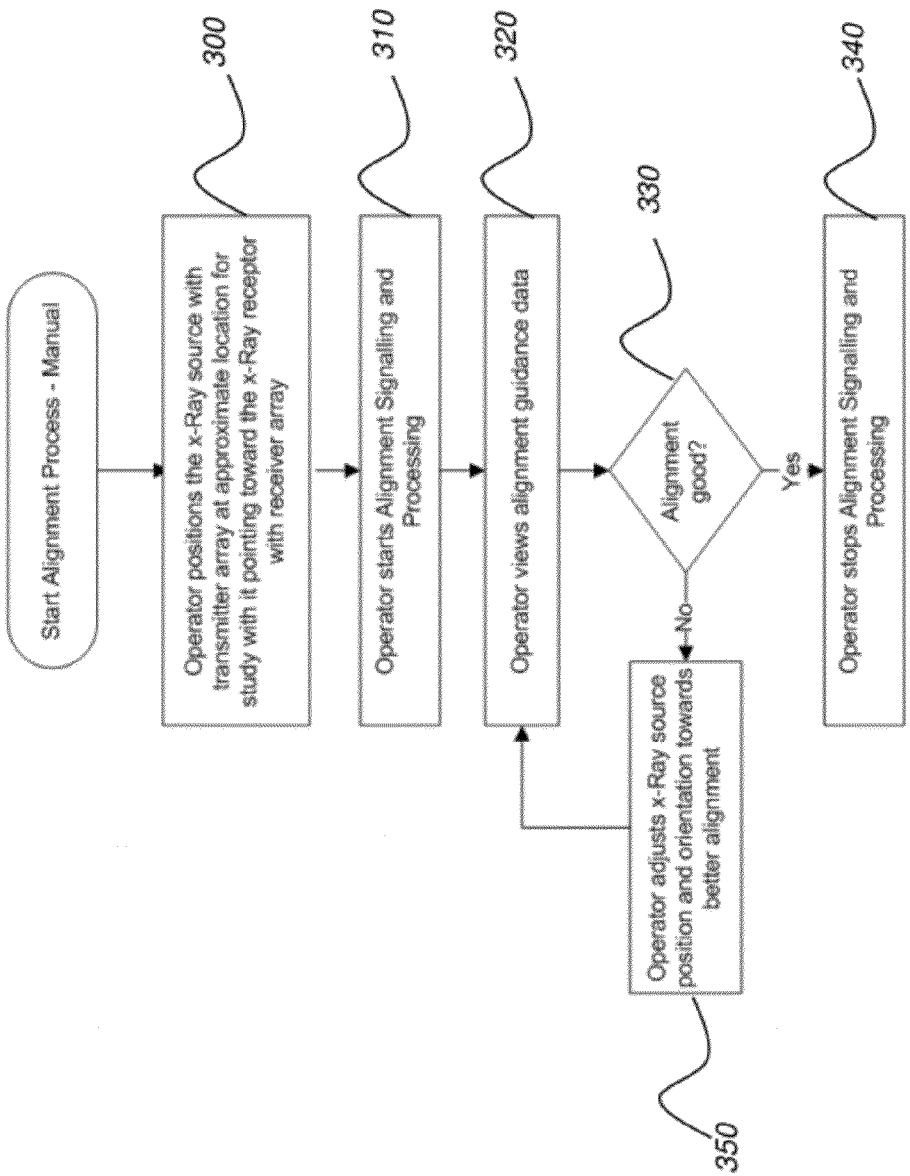
FIG. 16B is a logic flow diagram that shows the operation sequence for alignment using the apparatus of the present invention.

The flow diagram of FIG. 16B shows an operation sequence for alignment that can use or be implemented in exemplary apparatus embodiments herein. In a positioning step 300, the operator positions radiation source 20 pointing generally toward receiver 10, which is positioned behind the patient. The operator then enters a command that initiates repeating cycles of field generation and processing. Field generation and processing step 310 provides automatic generation of the sync signal 86 and magnetic field from each respective emitter apparatus T1 and T2 in sequence and sensing and processing of each received signal from sensor element 42, using the circuitry and signal sequence described with reference to FIGS. 14A through 15C. In an assessment step 320, the operator views displayed guidance data for readjustment of x-ray source 20 position. If adjustment is needed, an adjustment step 350 is executed and assessment step 320 repeated as shown. If a decision step 330 indicates success, alignment signaling and processing ends in a termination step 340. In the processing sequence, each respective emitter apparatus T1, T2 can be individually energized, in sequence, over substantially non-overlapping time intervals, with the cycle initiated and repeated as many times as controlled by control circuit such as control processor 202 (FIG. 14A). With each generation of a time-varying magnetic field by either emitter apparatus T1 or T2, some or all of the sensor elements 42 can be sensed for received signal.

Figure 17:
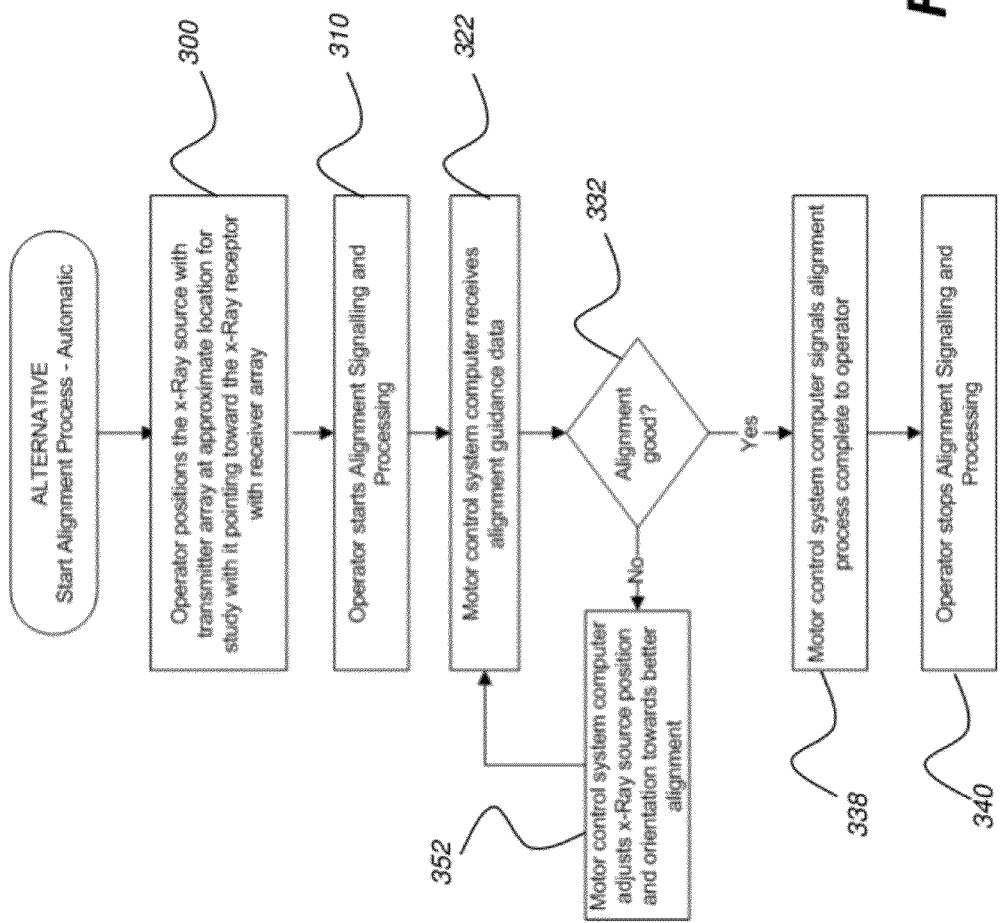
FIG. 17 is a logic flow diagram that shows an alternate sequence for automated alignment using the apparatus of the present invention.

Automated processing uses control logic to provide motor control signals for adjusting the position of radiation source 20. The flow diagram of FIG. 17 shows an alternate sequence for automated alignment that can use an apparatus embodiment. In a positioning step 300, the operator positions radiation source 20 pointing generally toward receiver 10 position behind the patient. The operator then enters a command that initiates a field generation and processing step 310 that provides automatic generation of the magnetic field from each respective emitter apparatus T1, T2 in sequence and sensing and processing of each received signal from sensor element 42, using the circuitry and signal sequence described with reference to FIGS. 14A through 15C. In an automated assessment step 322, control logic in control logic processor 48 or local to holder 46 or other component then determines what adjustments are needed. If a decision step 332 indicates success, a reporting step 338 indicates this to the operator. Alignment signaling and processing ends in a termination step 340. If adjustment is needed, an automated adjustment step 352 is executed by control logic and assessment step 322 is repeated as shown.

Figure 18:
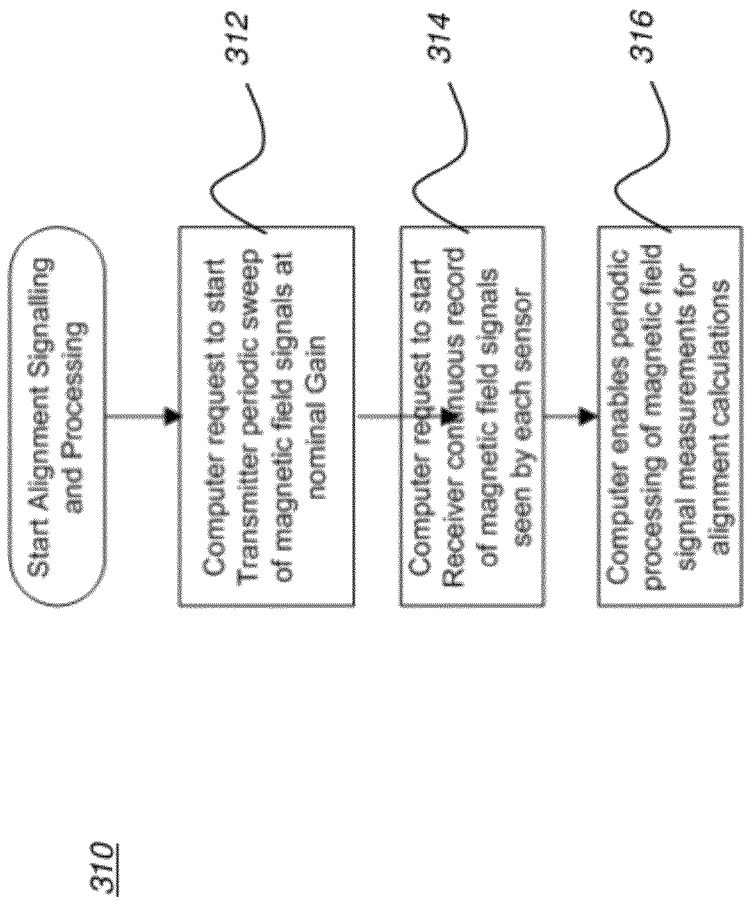
FIG. 18 is a logic flow diagram that shows how control logic executes a field generation and processing step according to an embodiment of the present invention.

The flow diagram of FIG. 18 shows how control logic executes field generation and processing step 310 according to another exemplary embodiment. In a signal initiation step 312, emitter circuit 200 is instructed to begin generation of the emitted signal from each field generation element 42 in sequence. In a sensing request step 314, the sensing apparatus 220 components are polled to obtain the sensed signals. A processing step 316 then executes to continuously obtain and process the sensed signal output from sensing apparatus 220.

Figure 19:
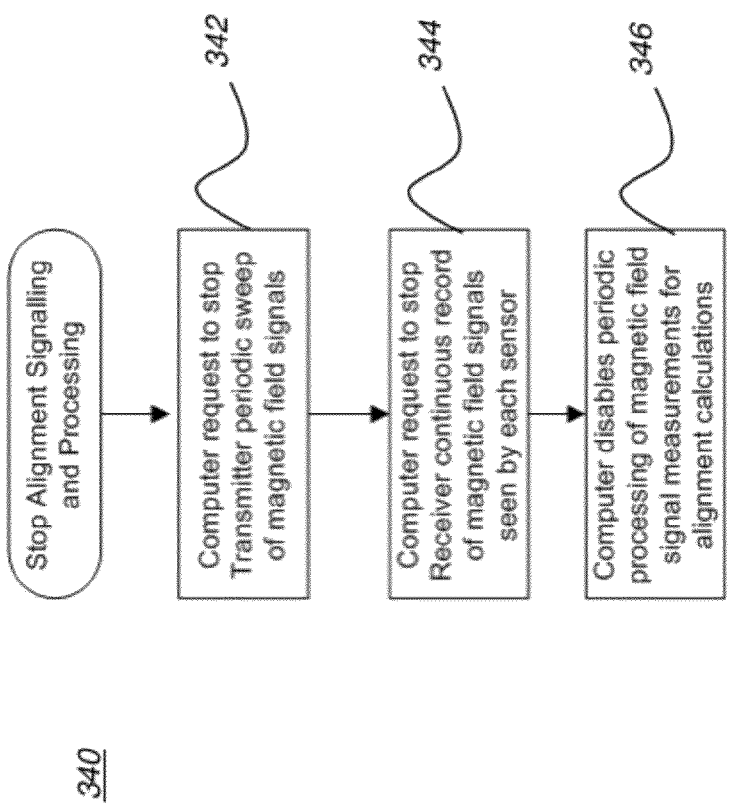
FIG. 19 is a logic flow diagram that shows processing for termination step according to an embodiment of the present invention.

The flow diagram of FIG. 19 shows processing for termination step 340 according to an exemplary embodiment. Three request steps 342, 344, and 346 are sent, to respectively de-activate field generation, magnetic field vector sensing, and periodic processing of received sensor element data, respectively.

Figure 20:
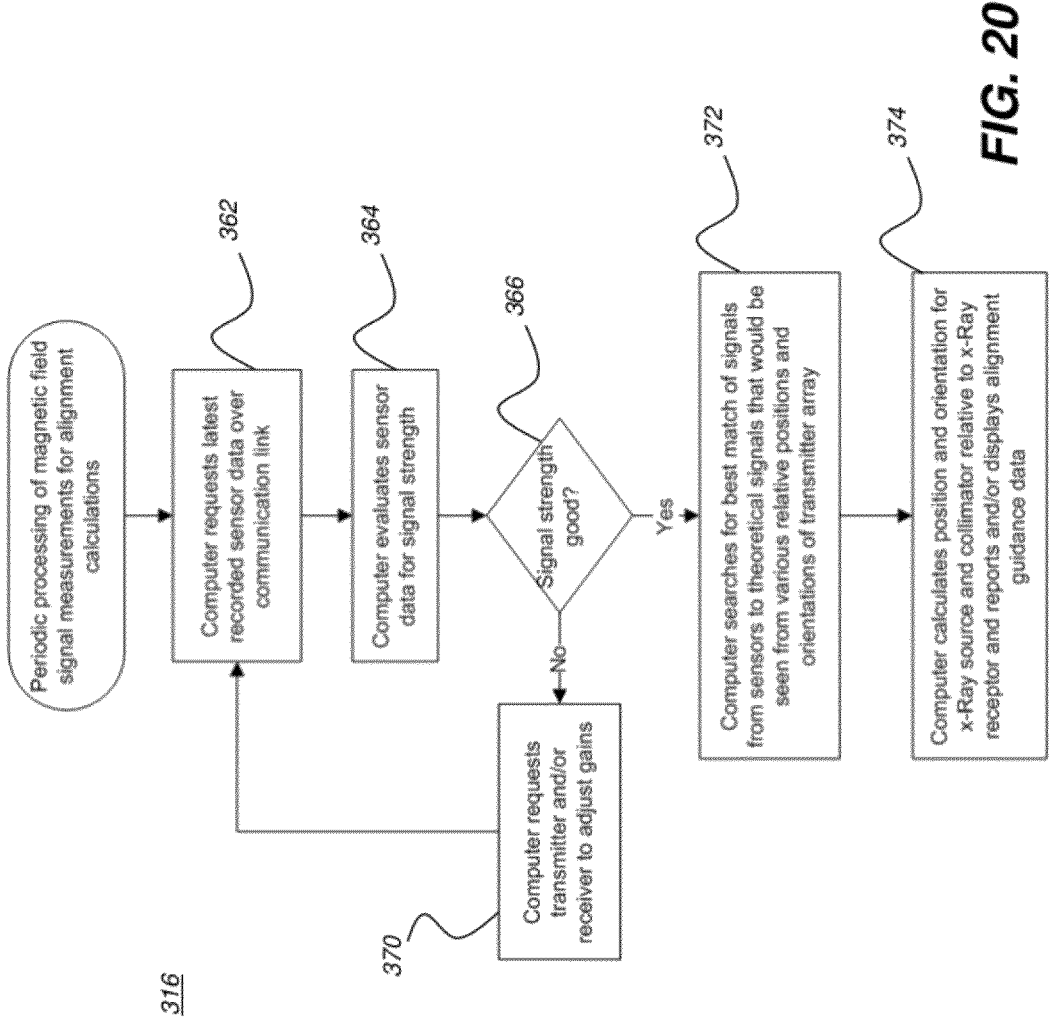
FIG. 20 is a logic flow diagram that shows periodic processing of sensor data according to an embodiment of the present invention.

The flow diagram of FIG. 20 shows processing step 316 for periodic processing of sensor data from sensing apparatus 220 according to an exemplary embodiment. In a request step 362, the computer or control logic processor 48 prompts sensing apparatus 220 for sensor data. An evaluation step 364 checks the signal strength. In a decision step 366, signal strength is compared against a desired threshold or other measure to determine whether or not to adjust either emitter circuit 200 output power or gain circuitry on sensing apparatus 220 in an adjustment request step 370. When signal strength is acceptable, control logic acquires the time-varying signals from each sensor element 42 in sensing apparatus 220.

In an alignment matching step 372, control logic compares the acquired signals against a mathematical model of theoretical phase and amplitude for the relative spatial disposition, including orientation and distance, of receiver 10 relative to source 20 until a best-fit match is identified. This match then provides the data needed to closely approximate the relative positions. A reporting step 374 then provides adjustment guidance to the operator, such as using the display screens described previously. It should be noted that processing step 316 continues during operator adjustment of x-ray source 20 position, updating the position report that is provided as the operator corrects the source positioning.

In practice, when the sensor elements 42 are attached to the grid frame and the whole assembly that includes receiver 10 is placed on a patient bed for imaging, the metallic structure of the bed itself, or of other types of surrounding metal structure associated with the patient's bed, can present interference to the alignment system. The level of interference varies with bed type, position and orientation of the frame on the bed, angle of the movable sections of the bed, and relative proximity of the alignment emitter.

This interference related to the bed structure can be caused by magnetic fields from eddy currents induced by the primary emitter fields in electrically conductive surfaces. A metal sheet surface can act as a magnetic "mirror" for the primary emitter fields. In addition, eddy currents tend to propagate toward perimeter edges of the sheet. This can cause intensified fields near the edges that potentially produce more interference. The interference can also be caused by magnetic fields from currents induced in electrically conductive loops, such as sections of the metal support structure and metal bed rails. Further, the interference can be caused by magnetic field distortion from ferrous metals that are disposed anywhere near the path of magnetic fields that are emitted by the alignment system emitter apparatus T and measured by the sensing apparatus R coils. The electric currents that are induced in the conductive metal surfaces and loops by magnetic fields from the emitters have surrounding fields that can also be detected by the sensor elements. Nearby ferrous metals can alter the normal expected path for magnetic field lines between the emitter apparatus and the sensing apparatus. These types of interference can cause phase shifts and amplitude modifications to the signals being observed by the grid frame sensors. This can result in measurement error of the alignment system.

Figure 21:
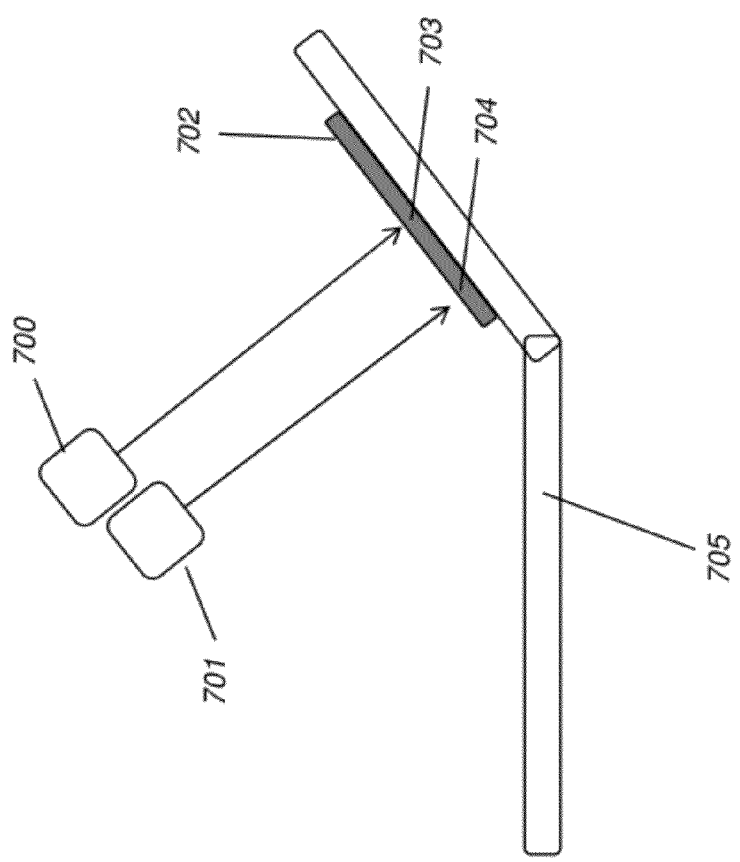
FIG. 21 is a side view schematic that shows measurement considerations related to a metal patient bed.

The interference caused in this manner can be mitigated using any of a number of methods. One method is to apply compensation based on empirical data. For example, FIG. 21 shows that when an image receiver in a grid frame 702 is placed on a semi-erected metallic bed 705, a reported radiation source position 701 can be slightly lower than an actual radiation source position 700. Actual and reported center x-ray positions 703 and 704 respectively differ.

Figure 22:
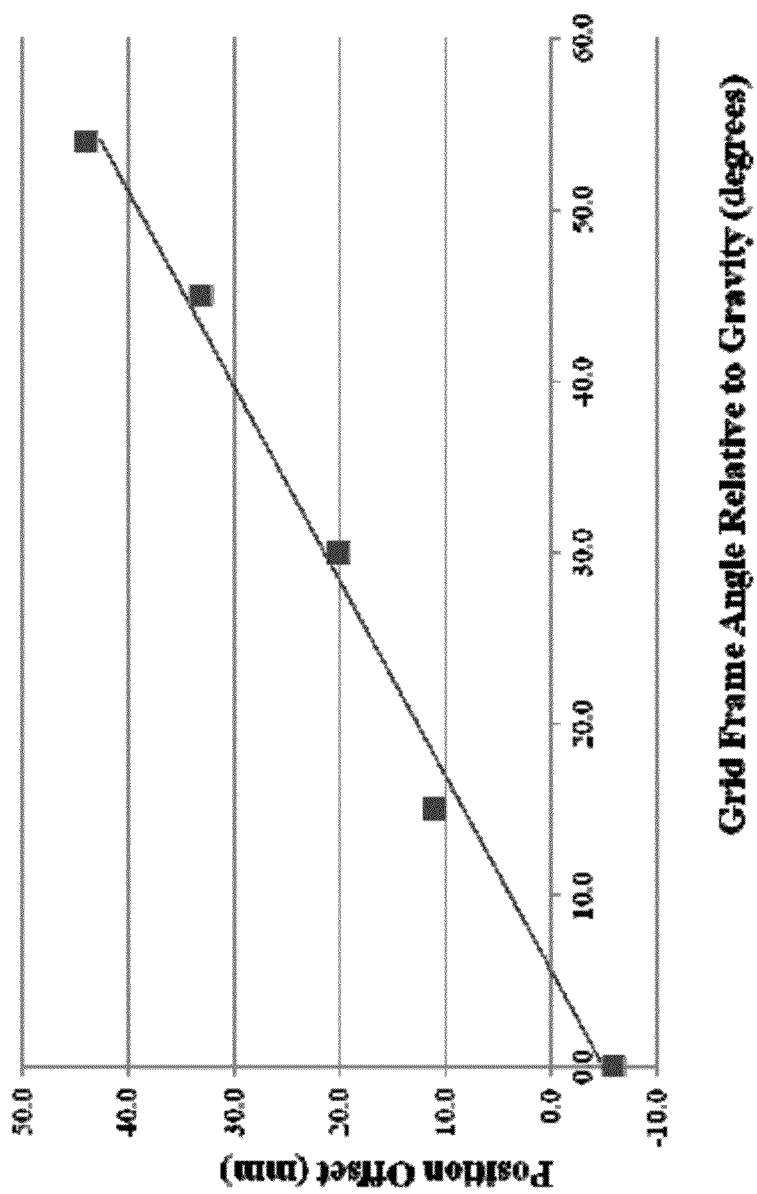
FIG. 22 is a graph that relates relative position offset to grid frame angle.

The graph of FIG. 22 shows the amount of vertical displacement between reported and actual radiation source positions as a function of the grid frame angle relative to gravity. For this particular case the relationship can be approximated as a linear function of the grid frame angle, which can be measured by an inclinometer or accelerometer etc that is attached to the grid frame. The compensation angle is added on top of the reported radiation source position so as to achieve the compensated values.

Another method embodiment to mitigate interference from the patient's bed and other surrounding structures is selective use of sensors that are least likely to be affected by the metallic structures. Experimentally, it has been found that proximity to the metal structure increases interference effects; the closer the sensor is to the metal structure, the more likely the sensor is to encounter higher interference. Referring to FIG. 21, for example, sensors closest to the bed frame are subject to higher interference. The alignment accuracy can be improved by ignoring sensors that are more susceptible to interference due to their relative position with respect to the bed frame, when there are still enough of sensors remaining for calculation or, alternately, to weight sensor measurement data accordingly.

It should be observed that a number of component arrangements are possible for emitter and sensing apparatus. For example, while orthogonal sensor element placement has advantages and is generally straightforward, other angular relationships could be used between sensor elements that receive the same signal, with corresponding changes in how position is computed. In practice, angles should differ from one sensor element to the next by at least ten degrees. More than two sensor elements are generally grouped together for detecting the same generated magnetic field.

Operational modifications can also be made in exemplary embodiments herein. For example, while sine and cosine signal processing is familiar and straightforward, other types of periodic signals could be used, such as repeated triangular or square waves, for example. Even non-periodic waveforms could be used if there is a way for the signal processor to identify and correlate them with known signatures. The use of a carrier signal has advantages for allowing the sensor elements in sensing apparatus R to be tuned to the emitter carrier frequency. However, the use of a carrier signal frequency is optional.

For triangulation between the x-ray source and receiver, at least one emitter apparatus T is needed, with at least three sensors as part of sensing apparatus R. Exclusive pairing of sensor elements to a specific emitter is not required. All sensor elements can be used to provide signals from each emitter T. Advantageously, no pointing vector is needed; sufficient information for positioning within the standard six DOF is provided by a combination of at least six measurements, obtained from either one emitter (T) or two (T1, T2), wherein phase and amplitude at one sensor element can be considered as separate measurements for this purpose.

An embodiment of the present invention provides an apparatus for aligning a radiation source with an image receiver having at least a first transmitter apparatus that is energizable to generate, about itself, a magnetic field having a fixed-position field pattern and having a time-varying vector direction at a predetermined frequency and a sensing apparatus with a plurality of sensor elements, wherein each of the plurality of sensor elements provides a sensor signal at the predetermined frequency of the time-varying magnetic field and wherein at least two of the sensor signals from the plurality of sensor elements differ from each other in phase or magnitude or both. There is a signal generation circuit that generates an output signal according to the plurality of sensor signals, wherein the output signal is indicative of the position and orientation of the sensing apparatus relative to the at least the first transmitter apparatus. The at least first transmitter apparatus is coupled to either one of the radiation source and the image receiver and the sensing apparatus is coupled to the other one of the radiation source and the image receiver.

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only. The scope of the invention is indicated by the appended claims, and all changes that come within the meaning and range of equivalents thereof are intended to be embraced therein.

The invention claimed is:

1. A method for aligning a radiation source with a portable image receiver in a radiographic imaging system, the method comprising:
generating a magnetic field with a predetermined field pattern and with a time-varying vector direction at a predetermined frequency from an emitter apparatus that is coupled to the radiation source, wherein the generated magnetic field further comprises a synchronization signal;
obtaining sensed signals from the magnetic field from a sensing apparatus that is coupled to the image receiver, wherein the sensing apparatus comprises three or more sensor elements, wherein at least two of the sensor elements are arranged at different angles relative to each other and are disposed outside the imaging area of the image receiver; and
providing an output signal indicative of an alignment adjustment according to the amplitude and phase of the obtained sensed signals relative to the synchronization signal.

2. The method of claim 1 wherein the output signal is further indicative of a distance between the emitter apparatus and the sensing apparatus according to the sensed output signals.

3. The method of claim 1 wherein the magnetic field is a first magnetic field, the predetermined field pattern is a first predetermined field pattern, the time-varying vector direction at the predetermined frequency is a first time-varying vector direction at a first predetermined frequency, the emitter apparatus is a first emitter apparatus, and the synchronization signal is a first synchronization signal, the method further comprising;
generating a second magnetic field with a second predetermined field pattern and with a second time-varying vector direction at a second predetermined frequency from a second emitter apparatus that is coupled to the radiation source, wherein the second generated magnetic field further comprises a second synchronization signal.

4. The method of claim 3 wherein the first and second predetermined frequencies are the same.

5. The method of claim 3 further comprising displaying the alignment adjustment,
wherein generating the first magnetic field comprises energizing a first emitter coil and a second emitter coil at the same frequency, and wherein the first and second emitter coils are substantially orthogonal to each other.

6. The method of claim 1 wherein generating the magnetic field further comprises generating a carrier signal.

7. The method of claim 1 wherein generating the magnetic field further comprises energizing a motor.

8. The method of claim 1 wherein obtaining the sensed signals further comprises iteratively comparing the obtained sensed signals against a mathematical model of theoretical phase and amplitude for spatial disposition of the receiver relative to the source until a best-fit match is identified.

9. The method of claim 1 further comprising processing the provided output signal to compensate for interference from metal structures associated with a patient's bed.

10. The method of claim 1 wherein providing the output signal indicative of the alignment adjustment comprises weighting the obtained sensed signals according to locations of one or more of the sensor elements relative to a patient's bed.

11. The method of claim 1 wherein providing the output signal comprises ignoring the obtained sensed signal from one or more of the sensor elements according to locations of the one or more of the sensor elements relative to a patient's bed.

12. An apparatus for aligning a radiation source in a radiographic imaging system with a portable image receiver, the apparatus comprising:
a first emitter apparatus coupled to the radiation source, wherein the first emitter apparatus comprises first and second coils and is energizable to generate a first magnetic field having a first predetermined field pattern and having a first time-varying vector direction at a first predetermined frequency;

a control circuit that energizes the first emitter apparatus to provide a first synchronization signal followed by the first predetermined field pattern;

a sensing apparatus that comprises a plurality of sensor elements, spaced apart from each other and peripheral to the image receiver, wherein each of the plurality of sensor elements provides a sensor signal at the first predetermined frequency of the first time-varying magnetic field and wherein at least two of the sensor signals from the plurality of sensor elements differ from each other in at least one of phase and magnitude relative to the first synchronization signal; and a signal generation circuit that generates an output signal according to the plurality of sensor signals, wherein the output signal is indicative of the position and orientation of the sensing apparatus relative to the emitter apparatus.

13. The apparatus of claim 12 further comprising:

a second emitter apparatus coupled to the radiation source, wherein the second emitter apparatus comprises third and fourth coils and is energizable to generate a second magnetic field having a second predetermined field pattern and having a second time-varying vector direction at a second predetermined frequency, and wherein the sensing apparatus further provides a sensor signal at the second predetermined frequency.

14. The apparatus of claim 12 wherein the first and second coils are disposed substantially orthogonal to each other or the first and second emitter coils differ from each other with respect to angular orientation by at least 10 degrees.

15. The apparatus of claim 12 further comprising an accelerometer coupled to either the first emitter apparatus or the sensing apparatus and wherein the accelerometer is in communication with the signal generation circuit, wherein the plurality of sensor elements comprise a coil, a Hall-effect device, a flux gate, a magneto-resistive sensor, a flux gate sensor, and a giant magneto-resistive sensor.

16. The apparatus of claim 12 wherein the first time-varying magnetic field is sinusoidal, and wherein the portable image receiver has an antiscatter grid.

17. The apparatus of claim 12 wherein one or more sensor elements of the plurality of sensor elements are aligned in parallel with a metal feature on the receiver.

18. The apparatus of claim 12 wherein at least one of the first or second emitter apparatus modulates a carrier signal that is at a frequency higher than the frequency of the first and second magnetic fields with time-varying vector directions.

19. An apparatus for aligning a radiation source in a radiographic imaging system with a portable image receiver, the apparatus comprising:

a first emitter apparatus and a second emitter apparatus coupled to the radiation source, wherein at least one of the first and second emitter apparatus comprises a motor and is energizable to generate:

(i) a magnetic field having a fixed-position field pattern and having a time-varying vector direction at a predetermined frequency; and (ii) a synchronization signal;

a control circuit that alternately energizes the first emitter apparatus and the second emitter apparatus over different, substantially non-overlapping time intervals;

a sensing apparatus that comprises an antiscatter grid between the imaging receiver and the radiation source, and a plurality of sensor elements, spaced apart from each other and disposed outside the imaging area of the image receiver, wherein each of the plurality of sensor elements provides a sensor signal at the predetermined frequency of the time-varying magnetic field and wherein at least two of the sensor signals from the plurality of sensor elements differ from each other in at least one of phase and magnitude relative to the synchronization signal; and a signal generation circuit that is energizable to generate an output signal according to the plurality of sensor signals, wherein the output signal is indicative of the position and orientation of the sensing apparatus relative to at least the first emitter apparatus.

20. The apparatus of claim 19 wherein the time-varying magnetic field is sinusoidal or periodic, wherein at least one of the first or second emitter apparatus modulates a carrier signal that is at a frequency higher than the frequency of the magnetic field with time-varying vector directions, wherein the imaging system further comprises an antiscatter grid.

* * * * *